(12) United States Patent
Slepnev

(10) Patent No.: US 7,081,339 B2
(45) Date of Patent: Jul. 25, 2006

(54) METHODS FOR VARIATION DETECTION

(75) Inventor: Vladimir I. Slepnev, Coventry, RI (US)

(73) Assignee: Primera BioSystems, Inc., Mansfield, MA (US)

( * ) Notice: Subject to any disclaimer, the term of this patent is extended or adjusted under 35 U.S.C. 154(b) by 501 days.

(21) Appl. No.: 10/387,286

(22) Filed: Mar. 12, 2003

(65) Prior Publication Data
US 2003/0235844 A1   Dec. 25, 2003

Related U.S. Application Data

(60) Provisional application No. 60/372,045, filed on Apr. 12, 2002.

(51) Int. Cl.
*C12Q 1/68* (2006.01)
*C12P 19/34* (2006.01)

(52) U.S. Cl. .......................................... 435/6; 435/91.2
(58) Field of Classification Search .................... 435/6, 435/91.2, 91.52
See application file for complete search history.

(56) References Cited

U.S. PATENT DOCUMENTS

| | | | |
|---|---|---|---|
| 5,691,146 A | 11/1997 | Mayrand | 435/6 |
| 6,221,600 B1 | 4/2001 | MacLeod | 435/6 |
| 6,482,615 B1 | 11/2002 | Tal et al. | 435/91.2 |
| 6,495,326 B1 | 12/2002 | Kurane et al. | 435/6 |
| 6,531,282 B1 | 3/2003 | Dau et al. | 435/6 |
| 2002/0028452 A1 | 3/2002 | Wittwer et al. | |

OTHER PUBLICATIONS

Sanchez-Vega et al., Laboratory Investigation 82(1), 345A (Jan. 2002).*
Sanchez-Vega et al., J. Mol. Diagnostics 4(4), 223-229 (Nov. 2002).*
International Search Report of International Application No. PCT/US03/37420.
Holland, et al., "Detection of specific polymerase chain reaction product by utilizing the 5'-3'exonuclease activity of *Thermus aquaticus* DNA polymerase", 1991, Proc. Natl. Acad. Sci. USA 88:7276-7280.
Borson, et al., "Direct Quantitation of RNA Transcripts by Competitive Single-Tube RT-PCR and Capillary Electrophoresis", 1998, Biotechniques 25: 130-7.
Rajcevic, et al., "Assessment of differential expression of oncogenes in gastric adenocarcinoma by fluorescent multiplex RT-PCR assay", 2001, Pflugers Arch., Eur. J. Physiol. 442 (6 Suppl 1): R190-2.

(Continued)

*Primary Examiner*—Kenneth R. Horlick
(74) *Attorney, Agent, or Firm*—Kathleen M. Williams; Mark J. FitzGerald; Edwards Angell Palmer & Dodge

(57) ABSTRACT

The invention relates to methods of monitoring the amplification of one or more nucleic acid sequences of interest. More particularly, the invention relates to methods of monitoring the amplification of sequences of interest in real time. The methods disclosed herein provide methods for monitoring the amplification of one sequence or two or more sequences from a single sample, as well as methods for monitoring the amplification of one or more than one sequence from two or more samples. The monitoring methods of the invention permit improved determination of the abundance of one or more target nucleic acids, especially target RNA species, in one or more original samples.

51 Claims, 8 Drawing Sheets

OTHER PUBLICATIONS

Odin et al., "Rapid method for relative gene expression determination in human tissues using automated capillary gel electrophoresis and multicolor detection", 1999, J. Chromatogr. B, 734:47-53.

George, et al., "Capillary electrophoresis methodology for identification of cancer related gene expression patterns of fluorescent differential display polymerase chain reaction", 1997, J. Chromatogr. B., 695: 93-102.

Omori, et al., "Comparative PCR: A Simple and Sensitive Method for Quantifying Low-Abundance mRNA Species", 2000, Genomics 67: 140-5.

O'Dorschner, et al., "Diagnosis of Five Spinocerebellar Ataxia Disorders by Multiplex Amplification and Capillary Electrophoresis", Journal of Molecular Diagnostics (2002), V. 4, No. 2, pp. 108-113.

Erdman, et al., "GeneScan Reverse Transcription-PCR Assay for Detection of Six Common Respiratory Viruses in Young Children Hospitalized with Acute Respiratory Illness", Journal of Clinical Microbiology (2003), V. 41, No. 9, pp. 4298-4303.

Li, et al., "Quantitative Polymerase Chain Reaction Using Capillary Electrophoresis with Laser-Induced Fluorescence Detection: Analysis of Duck Hepatitis B", Anal Bioannal Chem (2002), V. 374, pp. 269-273.

Martin, et al., "Automated Ribosomal DNA Fingerprinting by Capillary Electrophoresis of PCR Products", Analytical Biochemistry (1993), V. 214, pp. 182-189.

Odin, et al., "Rapid Method for Relative Gene Expression Determination in Human Tissues Using Automated Capillary Gel Electrophoresis and Multicolor Detection", Journal of Chromatography (1999), V. 734, pp. 47-53.

Lawrence, et al., "Evaluation of Semiautomated Multiplex PCR Assay for Determination of *Streptococcus pneumoniae* Serotypes and Serogroups" Journal of Clinical Microbiology (2003), V. 41, No. 2, pp. 601-607.

\* cited by examiner

Recovery of Quantitative difference

Two samples containing two different RNAs
Sample 1          Sample2
VS31    equal concentration
VS32    2.5 times more in sample2

Expected results:

RNA1
Threshold cycles (Ct) for both samples is equal

RNA2
Threshold cycle (Ct) for sample 2 (R) is less than
Threshold cycle (Ct) for sample 1 (F)

SEQUENCE LISTING

<160> NUMBER OF SEQ ID NOS: 9

<210> SEQ ID NO 1
<211> LENGTH: 24
<212> TYPE: DNA
<213> ORGANISM: Artificial sequence
<220> FEATURE:
<223> OTHER INFORMATION: Synthetic PCR primer that hybridizes to
      sequence in cloning vector pCDNA3 (Invitrogen)

<400> SEQUENCE: 1
atcgaaatta atacgactca ctat                                              24

<210> SEQ ID NO 2
<211> LENGTH: 24
<212> TYPE: DNA
<213> ORGANISM: Artificial sequence
<220> FEATURE:
<223> OTHER INFORMATION: Synthetic PCR primer that hybridizes to
      sequence in cloning vector pCDNA3 (Invitrogen)

<400> SEQUENCE: 2
agctctagca tttaggtgac acta                                              24

<210> SEQ ID NO 3
<211> LENGTH: 37
<212> TYPE: DNA
<213> ORGANISM: Artificial sequence
<220> FEATURE:
<223> OTHER INFORMATION: Sequence-tagged synthetic oligonucleotide
      primer used for reverse transcription.

<400> SEQUENCE: 3
aattccgcgc cgaataatat taagctctag catttag                                37

<210> SEQ ID NO 4
<211> LENGTH: 37
<212> TYPE: DNA
<213> ORGANISM: Artificial sequence
<220> FEATURE:
<223> OTHER INFORMATION: Sequence-tagged synthetic oligonucleotide
      primer used for reverse transcription.

<400> SEQUENCE: 4
aattcccggc ggattattta ttagctctag catttag                                37

<210> SEQ ID NO 5
<211> LENGTH: 19
<212> TYPE: DNA
<213> ORGANISM: Artificial sequence
<220> FEATURE:
<223> OTHER INFORMATION: Artificial sequence tag used in amplification

<400> SEQUENCE: 5
ccgcgccgaa taatattaa                                                    19

<210> SEQ ID NO 6
<211> LENGTH: 19
<212> TYPE: DNA
<213> ORGANISM: Artificial sequence
<220> FEATURE:
<223> OTHER INFORMATION: Artificial sequence tag used in amplification

<400> SEQUENCE: 6
cccggcggat tatttatta                                                    19

```
<210> SEQ ID NO 7
<211> LENGTH: 20
<212> TYPE: DNA
<213> ORGANISM: Artificial sequence
<220> FEATURE:
<223> OTHER INFORMATION: Synthetic PCR primer identical to the sequence
      present at the 5' end of the sample RNAs in Example 1.

<400> SEQUENCE: 7
ccatacgacg tcccagacta                                               20

<210> SEQ ID NO 8
<211> LENGTH: 33
<212> TYPE: DNA
<213> ORGANISM: Artificial sequence
<220> FEATURE:
<223> OTHER INFORMATION: Synthetic oligonucleotide primer used for
      reverse transcription in Example 2.

<400> SEQUENCE: 8
ccgcgccgaa taatattaag ctctagcatt tag                                33

<210> SEQ ID NO 9
<211> LENGTH: 33
<212> TYPE: DNA
<213> ORGANISM: Artificial sequence
<220> FEATURE:
<223> OTHER INFORMATION: Synthetic oligonucleotide primer used for
      reverse transcription in Example 2.

<400> SEQUENCE: 9
cccggcggat tatttattag ctctagcatt tag                                33
```

METHODS FOR VARIATION DETECTION

This U.S. patent application claims the priority of U.S. provisional Application No. 60/372,045 filed Apr. 12, 2002.

BACKGROUND

The Polymerase Chain Reaction (PCR), with its sensitive and selective amplification of specific nucleic acid sequences has become a research tool of almost unparalleled importance, with applications in, for example, cloning, gene expression analysis, DNA sequencing, genetic mapping and diagnostics.

While one of the major attributes of the PCR process is its speed, often amplifying target sequences within minutes to hours, there is a need for real-time monitoring of PCR reactions. This is especially true for quantitative PCR methods, which seek to correlate the abundance of a detectable PCR product with the abundance of the template in the sample from which it was amplified. In those methods, because PCR amplification reaches a plateau or stationary phase in which the abundance of product no longer reflects the abundance of original template, and because sequence-specific variations in amplification efficiency are magnified by the process itself, it is often important to be able to visualize the amount of a target product at a given point in the amplification.

Moreover, real time monitoring of an amplification reaction permits far more accurate quantification of starting target DNA concentrations in multiple-target amplifications, because the relative values of close concentrations can be resolved by taking into account the history of the relative concentration values during the reaction. Real time monitoring also permits the efficiency of the amplification reaction to be evaluated, which can indicate whether reaction inhibitors are present in a sample.

Holland et al. (1991, Proc. Natl. Acad. Sci. U.S.A. 88: 7276–7280), U.S. Pat. No. 5,210,015 and others have disclosed fluorescence-based approaches to provide real time measurements of amplification products during PCR. Such approaches have either employed intercalating dyes (such as ethidium bromide) to indicate the amount of double-stranded DNA present or they have employed probes containing fluorescence-quencher pairs (also referred to as the "Taq-Man" approach) where the probe is cleaved during amplification to release a fluorescent molecule the concentration of which is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear.

The Taq-Man approach uses an oligonucleotide probe containing a reporter molecule—quencher molecule pair that specifically anneals to a region of a target polynucleotide "downstream", i.e. in the direction of extension of primer binding sites. The reporter molecule and quencher molecule are positioned on the probe sufficiently close to each other such that whenever the reporter molecule is excited, the energy of the excited state nonradiatively transfers to the quencher molecule where it either dissipates nonradiatively or is emitted at a different emission frequency than that of the reporter molecule. During strand extension by a DNA polymerase, the probe anneals to the template where it is digested by the 5' to 3' exonuclease activity of the polymerase. As a result of the probe being digested, the reporter molecule is effectively separated from the quencher molecule such that the quencher molecule is no longer close enough to the reporter molecule to quench the reporter molecule's fluorescence. Thus, as more and more probes are digested during amplification, the number of reporter molecules in solution increases, thus resulting in an increasing number of unquenched reporter molecules which produce a stronger and stronger fluorescent signal.

The other most commonly used real time PCR approach uses the so-called "molecular beacons" technology. This approach is also based upon the presence of a quencher-fluorophore pair on an oligonucleotide probe. In the beacon approach, a probe is designed with a stem-loop structure, and the two ends of the molecule are labeled with a fluorophore and a quencher of that fluorophore, respectively. In the absence of target polynucleotide, the complementary sequences on either end of the molecule permit stem formation, bringing the labeled ends of the molecule together, so that fluorescence from the fluorophore is quenched. In the presence of the target polynucleotide, which bears sequence complementary to the loop and part of the stem structure of the beacon probe, the intermolecular hybridization of the probe to the target is energetically favored over intramolecular stem-loop formation, resulting in the separation of the fluorophore and the quencher, so that fluorescent signal is emitted upon excitation of the fluorophore. The more target present, the more probe hybridizes to it, and the more fluorophore is freed from quenching, providing a read out of the amplification process in real time.

Both the Taq-Man and Beacons technologies are limited in that specialized individual double-labeled probes need to be generated for each gene target sequence.

The ability to "multiplex" (perform analysis of multiple genes in the same amplification reaction) in real-time amplification is limited to the optical separation of the commonly used fluorescence dyes. Typically, the maximal number of genes that can be analyzed in multiplex real-time reaction is limited to 4. In addition, the quantitative analysis often can be complicated by the presence of non-specific products of amplification Capillary electrophoresis has been used to quantitatively detect gene expression. Rajevic at el. (2001, Pflugers Arch. 442(6 Suppl 1):R190–2) discloses a method for detecting differential expression of oncogenes by using Seven pairs of primers for detecting the differences in expression of a number of oncogenes simultaneously. Sense primers were 5' end-labelled with a fluorescent dye and multiplex fluorescent RT-PCR results were analyzed by capillary electrophoresis on ABI-PRISM 310 Genetic Analyzer. Borson et al. (1998, Biotechniques 25:130–7) describes a strategy for dependable quantitation of low-abundance mRNA transcripts based on quantitative competitive reverse transcription PCR (QC-RT-PCR) coupled to capillary electrophoresis (CE) for rapid separation and detection of products. George et al., (1997, J. Chromatogr. B. Biomed. Sci. Appl. 695: 93–102) describes the application of a capillary electrophoresis system (ABI 310) to the identification of fluorescent differential display generated EST patterns. Odin et al. (1999, J. Chromatogr. B. Biomed. Sci. Appl. 734:47–53) describes an automated capillary gel electrophoresis with multicolor detection for separation and quantification of PCR-amplified cDNA.

Omori et al. (2000, Genomics 67:140–5) measures and compares the amount of commercially purchased α-globin mRNA by competitive PCR in two independently reverse transcribed cDNA samples using oligo(dT) primers. The oligo(dT) primers share a 3' oligo(dT) sequence and a 5' common sequence. In addition the oligo(dT) primer for each sample also contains a unique 29 nucleotide sequence between the 3' oligo(dT) sequence and the 5' common sequence. After the synthesis of first strand cDNA, PCR is performed to amplify the cDNA using a gene-specific primer and a uniquely labeled primer complementary to the common sequence. The amplified PCR products are then analyzed by spotting onto a detection plate of a fluorescence scanner.

There is a need in the art for real-time PCR methods that permit the visualization of the entire range of products in the PCR reaction. There is a further need in the art for real-time PCR methods that permit the monitoring of the amplification process for multiple amplification products in the same reaction, as well as a need for methods that monitor the amplification process for multiple products in the same reaction in a sample-specific manner.

SUMMARY OF THE INVENTION

The invention relates to methods of monitoring the amplification of one or more nucleic acid sequences of interest. More particularly, the invention relates to methods of monitoring the amplification of sequences of interest in real time. The methods disclosed herein provide methods for monitoring the amplification of one sequence or two or more sequences from a single sample, as well as methods for monitoring the amplification of one or more than one sequence from two or more samples. The monitoring methods of the invention permit improved determination of the abundance of one or more target nucleic acids, especially target RNA species, in one or more original samples.

The invention encompasses a method for monitoring the amplification of a nucleic acid sequence of interest, the method comprising: (a) contacting a nucleic acid sample with a first and a second oligonucleotide primer, wherein the first oligonucleotide primer specifically hybridizes with a nucleic acid molecule comprising the nucleic acid sequence of interest, and the second oligonucleotide primer specifically hybridizes with the complementary strand of the nucleic acid sequence of interest, wherein the primer extension product of one oligonucleotide primer, when separated from its complement, can serve as a template for the synthesis of the extension product of the other primer, and wherein at least one of the first and the second primers is labeled and preferably, labeled with a detectable marker; (b) subjecting the mixture resulting from step (a) to an amplification regimen, the regimen comprising at least two cycles of nucleic acid strand separation, oligonucleotide primer annealing, and polymerase extension of annealed primers; and (c) removing an aliquot of the mixture, separating nucleic acid molecules in the aliquot, and detecting incorporation of the at least one detectable marker, wherein the removing is performed during the cycling regimen of step (b), following at least one of the cycles, wherein the separating nucleic acid molecules step and the detecting incorporation step is performed in real time during the regimen of step (b) and wherein the detection permits the monitoring of the amplification in real time.

In one embodiment, the detectable label comprises a light-absorbing dye, a fluorescent dye or a radioactive label. In a preferred embodiment, the detectable label comprises a fluorescent dye.

In one embodiment, step (c) is performed after each cycle in the amplification regimen.

In another embodiment, the step of separating nucleic acid molecules comprises capillary electrophoresis.

In another embodiment, the sample comprises products of a reverse-transcription reaction.

In another embodiment, steps (a)–(c) are performed in a modular apparatus comprising a thermal cycler, a sampling device, a capillary electrophoresis device and a fluorescence detector. In a preferred embodiment, the modular device comprises a robotic arm.

In another embodiment, the monitoring permits the determination of the abundance of nucleic acid comprising the sequence of interest in the sample.

The invention further encompasses a method for monitoring the amplification of a set of nucleic acid sequences of interest, the method comprising: (a) contacting a nucleic acid sample in a reaction vessel with a set of pairs of oligonucleotide primers, wherein: each pair comprises a first oligonucleotide primer that specifically hybridizes with a nucleic acid molecule comprising the nucleic acid sequence of interest, and a second oligonucleotide primer that specifically hybridizes with the complementary strand of the nucleic acid sequence of interest, wherein the primer extension product of one oligonucleotide primer, when separated from its complement, can serve as a template for the synthesis of the extension product of the other primer; each pair of oligonucleotides is specific for one nucleic acid sequence of interest; each oligonucleotide primer pair in the set is selected so that it generates a distinctly sized amplification product in a subsequent amplification regimen; and one oligonucleotide in each the pair of oligonucleotides is detectably labeled; (b) subjecting the mixture resulting from step (a) to an amplification regimen comprising at least two iterative cycles of nucleic acid strand separation, oligonucleotide primer annealing and polymerase extension of annealed primers, wherein during the amplification regimen, following at least one of the iterative cycles, an aliquot of the mixture is removed from the reaction vessel and nucleic acid molecules in the aliquot are separated; (c) detecting the incorporation of detectable label in a distinctly sized primer extension product present in the aliquot, wherein the detecting provides a real time profile of the amplification of the nucleic acid sequences of interest.

In one embodiment, the detectable label comprises a light-absorbing dye, a fluorescent dye or a radioactive label. In a preferred embodiment, the detectable label comprises a fluorescent dye.

In one embodiment, an aliquot is removed and nucleic acid molecules in the aliquot are separated and detected after each cycle in the amplification regimen.

In another embodiment, the step of separating nucleic acid molecules comprises capillary electrophoresis.

In another embodiment, the sample comprises products of a reverse-transcription reaction.

In another embodiment, steps (a)–(c) are performed in a modular apparatus comprising a thermal cycler, a sampling device, a capillary electrophoresis device and a fluorescence detector. In a preferred embodiment, the modular apparatus comprises a robotic arm.

In another embodiment, the monitoring permits the determination of the abundance of nucleic acids comprising the set of nucleic acid sequences of interest in the sample.

The invention further encompasses a method of monitoring the amplification of a set of nucleic acid sequences of interest, the method comprising: (a) synthesizing a plurality of reverse transcription products by extension of a reverse transcription primer annealed to a template nucleic acid sample, wherein each of the reverse-transcription products comprises a common sequence tag comprised by the reverse-transcription primer; (b) contacting the reverse-transcription products in a reaction vessel with (i) a set of oligonucleotide primers that recognize the set of nucleic acid sequences of interest, wherein each oligonucleotide primer is selected so that it generates a distinctly sized amplification product in a subsequent amplification regimen, and (ii) a detectably labeled oligonucleotide primer that recognizes the common sequence tag; (c) subjecting the mixture resulting from step (b) to an amplification regimen comprising at least two iterative cycles of nucleic acid strand separation, oligonucleotide primer annealing and polymerase extension of annealed primers, wherein during the amplification regimen, following at least one of the iterative cycles, an aliquot of the mixture is removed from the reaction vessel and nucleic acid molecules in the aliquot are separated; (d) detecting the incorporation of the detectably labeled oligonucleotide primer in a distinctly sized primer extension product present in the aliquot, wherein the detecting provides a profile of the amplification of the set of nucleic acid sequences of interest.

In one embodiment, the detectable label comprises a light-absorbing dye, a fluorescent dye or a radioactive label. In a preferred embodiment, the detectable label comprises a fluorescent dye.

In one embodiment, an aliquot is removed and nucleic acid molecules in the aliquot are separated and detected after each cycle in the amplification regimen. In a preferred embodiment, for each aliquot removed, a reaction is replenished with an aliquot of reaction mixture (comprising primers, nucleotides and polymerase) to compensate for the volume loss due to sample removal.

In another embodiment, the aliquot removal, separating and detecting steps permit the real-time monitoring of the amplification.

In another embodiment, the step of separating nucleic acid molecules comprises capillary electrophoresis.

In another embodiment, the steps (a)–(d) are performed in a modular apparatus comprising a thermal cycler, a sampling device, a capillary electrophoresis device and a fluorescence detector. In a preferred embodiment, the modular device comprises a robotic arm.

In another embodiment, the monitoring permits the determination of the abundance of nucleic acids comprising the set of nucleic acid sequences of interest in the sample.

The invention further encompasses a method for comparing the expression of a nucleic acid sequence of interest between a set of samples, the method comprising: (a) separately synthesizing a plurality of first strand cDNAs from each member of the set of samples using, for each sample, an oligonucleotide primer comprising a different sample-specific sequence tag; (b) mixing equal amounts of the first strand cDNAs from step (a); (c) contacting the mixture resulting from step (b) in a reaction vessel with oligonucleotide primers comprising: (i) a separate, distinguishably detectably labeled oligonucleotide primer corresponding to each sample-specific sequence tag used in step (a), wherein the primer comprises sufficient sequence comprised by the sample specific sequence tag to permit specific annealing of the primer to a nucleic acid molecule comprising sequence complementary to the sample-specific tag; and (ii) an oligonucleotide primer comprising sufficient sequence complementary to the nucleic acid sequence of interest to permit specific annealing of the primer to a nucleic acid molecule comprising the sequence of interest; wherein the primers corresponding to the sample-specific sequence tags and the primer comprising sequence complementary to the nucleic acid sequence of interest generate primer extension products that, when separated from their complements, can serve as template for the synthesis of a primer extension product of the other primer; and (d) subjecting the mixture of step (c) to an amplification regimen comprising at least two iterative cycles of strand separation, oligonucleotide primer annealing, and polymerase extension of the annealed primers; (e) removing, during the amplification regimen, following at least one of the iterative cycles, an aliquot from the reaction vessel, separating nucleic acids in the aliquot and detecting primer extension products comprising distinguishably detectably labeled oligonucleotide primer corresponding to each sample-specific sequence tag, wherein the separating nucleic acid molecules and the detecting incorporation is performed in real time during the regimen of step (d) and wherein the detection permits the monitoring of the amplification in real time; (f) comparing the detectable signals from the labels corresponding to the sample-specific tags, thereby comparing the expression of the gene of interest between the samples.

In one embodiment, the detectable label comprises a light-absorbing dye, a fluorescent dye or a radioactive label. In a preferred embodiment, the detectable label comprises a fluorescent dye.

In one embodiment, the steps of removing an aliquot, separating nucleic acids in the aliquot and detecting primer extension products is performed after each cycle in the amplification regimen.

In another embodiment, the step of separating nucleic acid molecules comprises capillary electrophoresis.

In another embodiment, the steps (a)–(c) are performed in a modular apparatus comprising a thermal cycler, a sampling device, a capillary electrophoresis device and a fluorescence detector.

In another embodiment, the modular device comprises a robotic arm.

The invention further encompasses a method of monitoring the amplification of a set of nucleic acid sequences, the method comprising: (a) amplifying a set of nucleic acid sequences present in a set of reverse-transcription products wherein the amplifying comprises a regimen of at least two cycles of strand separation, oligonucleotide primer annealing and polymerase extension of the annealed primers, wherein each reverse transcription product in the set was made by extension of a reverse-transcription primer, the set of reverse transcription products comprising: one or more subsets of reverse-transcription products, wherein each subset comprises a plurality of reverse-transcription products from a single nucleic acid sample, wherein the members of each subset of reverse-transcription products comprise a sample-specific sequence tag incorporated into the reverse-transcription primer, wherein the amplifying comprises contacting the set of reverse-transcription products with two sets of oligonucleotide primers: (i) a set of gene-specific primers, wherein each gene specific primer in the set recognizes a specific nucleic acid sequence expressed in a nucleic acid sample, and wherein each gene specific primer in the set is selected so as to generate an amplification product that is distinct in size from amplification products generated with other gene specific primers in the set; and (ii) a set of sample specific primers, wherein each sample specific primer specifically hybridizes to a sample specific tag incorporated into a the reverse-transcription primer, and wherein each sample specific primer in the set of sample specific primers is distinguishably labeled; (b) during the regimen, following a primer extension step, removing an aliquot of the amplification mixture and separating nucleic acids in the aliquot; and (c) detecting incorporation of each sample specific primer in the aliquot; wherein the detecting monitors, in each sample, in real time, the amplification of the set of nucleic acids recognized by the set of gene specific primers.

In one embodiment, the detectable label comprises a light-absorbing dye, a fluorescent dye or a radioactive label. In a preferred embodiment, the detectable label comprises a fluorescent dye.

In one embodiment, the steps of removing an aliquot, separating nucleic acids in the aliquot and detecting primer extension products therein is performed after each cycle in the amplification regimen.

In another embodiment, the step of separating nucleic acid molecules comprises capillary electrophoresis.

In another embodiment, the steps (a)–(c) are performed in a modular apparatus comprising a thermal cycler, a sampling device, a capillary electrophoresis device and a fluorescence detector. In a preferred embodiment, the modular apparatus comprises a robotic arm.

In another embodiment, the monitoring permits the determination of the abundance of nucleic acids comprising the set of nucleic acid sequences of interest in a sample from which said reverse-transcription products are made.

Definitions

As used herein, the term "sample" refers to a biological material which is isolated from its natural environment and containing a polynucleotide. A "sample" according to the invention may consist of purified or isolated polynucleotide, or it may comprise a biological sample such as a tissue sample, a biological fluid sample, or a cell sample comprising a polynucleotide. A biological fluid includes blood, plasma, sputum, urine, cerebrospinal fluid, lavages, and leukophoresis samples. A sample of the present invention may be any plant, animal, bacterial or viral material containing a polynucleotide.

As used herein, an "oligonucleotide primer" refers to a polynucleotide molecule (i.e., DNA or RNA) capable of annealing to a polynucleotide template and providing a 3' end to produce an extension product which is complementary to the polynucleotide template. The conditions for initiation and extension usually include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer according to the invention may be single- or double-stranded. The primer is single-stranded for maximum efficiency in amplification, and the primer and its complement form a double-stranded polynucleotide. "Primers" useful in the present invention are less than or equal to 100 nucleotides in length, e.g., less than or equal to 90, or 80, or 70, or 60, or 50, or 40, or 30, or 20, or 15, or equal to 10 nucleotides in length.

As used herein, the term "specifically hybridizes" means that under given hybridization conditions a probe or primer hybridizes only to the target sequence in a sample comprising the target sequence. Given hybridization conditions include the conditions for the annealing step in an amplification regimen, i.e., annealing temperature selected on the basis of predicted Tm, and salt conditions suitable for the polymerase enzyme of choice.

As used herein, the term "nucleic acid sequence of interest" or "target sequence" refers to a nucleic acid sequence, in a sample, for which one wishes to determine the presence or abundance. The sequence of interest will most often be a transcript of an RNA expression unit or gene, but can be any nucleic acid sequence, e.g., a sequence comprised in a viral, bacterial, fungal or higher eukaryotic genome, or an artificial or synthetic sequence.

As used herein, the term "amplification regimen" means a process of specifically amplifying the abundance of a nucleic acid sequence of interest. An amplification regimen according to the invention comprises at least two, and preferably at least 5, 10, 15, 20, 25, 30, 35 or more iterative cycles of thermal denaturation, oligonucleotide primer annealing to template molecules, and nucleic acid polymerase extension of the annealed primers. Conditions and times necessary for each of these steps are well known in the art. Amplification achieved using an amplification regimen is preferably exponential, but can alternatively be linear. An amplification regimen according to the invention is preferably performed in a thermal cycler, many of which are commercially available.

As used herein, the term "strand separation" means treatment of a nucleic acid sample such that complementary double-stranded molecules are separated into two single strands available for annealing to an oligonucleotide primer. Strand separation according to the invention is achieved by heating the nucleic acid sample above its $T_m$. Generally, for a sample containing nucleic acid molecules in buffer suitable for a nucleic acid polymerase, heating to 94° C. is sufficient to achieve strand separation according to the invention. An exemplary buffer contains 50 mM KCl, 10 mM Tric-HCl (pH 8.8@ 25° C.), 0.5 to 3 mM $MgCl_2$, and 0.1% BSA.

As used herein, the term "primer annealing" means permitting oligonucleotide primers to hybridize to template nucleic acid strands. Conditions for primer annealing vary with the length and sequence of the primer and are based upon the calculated $T_m$ for the primer. Generally, an annealing step in an amplification regimen involves reducing the temperature following the strand separation step to a temperature based on the calculated $T_m$ for the primer sequence, for a time sufficient to permit such annealing. $T_m$ can be readily predicted by one of skill in the art using any of a number of widely available algorithms (e.g., Oligo™, Primer Design and programs available on the internet, including Primer3 and Oligo Calculator). For most amplification regimens, the annealing temperature is selected to be about 5° C. below the predicted $T_m$, although temperatures closer to and above the $T_m$ (e.g., between 1° C. and 5° C. below the predicted $T_m$ or between 1° C. and 5° C. above the predicted $T_m$) can be used, as can temperatures more than 5° C. below or above the predicted $T_m$ (e.g., 6° C. below, 8° C. below, 10° C. below or lower and 6° C. above, 8° C. above, or 10° C. above). Generally, the closer the annealing temperature is to the $T_m$, the more specific is the annealing. Time of primer annealing depends largely upon the volume of the reaction, with larger volumes requiring longer times, but also depends upon primer and template concentrations, with higher relative concentrations of primer to template requiring less time than lower. Depending upon volume and relative primer/template concentration, primer annealing steps in an amplification regimen can be on the order of 1 second to 5 minutes, but will generally be between 10 seconds and 2 minutes, preferably on the order of 30 seconds to 2 minutes.

As used herein, the term "polymerase extension" means the template-dependent incorporation of at least one complementary nucleotide, by a nucleic acid polymerase, onto the 3' end of an annealed primer. Polymerase extension preferably adds more than one nucleotide, preferably up to and including nucleotides corresponding to the full length of the template. Conditions for polymerase extension vary with the identity of the polymerase. The temperature of polymerase extension is based upon the known activity properties of the enzyme. In general, although the enzymes retain at least partial activity below their optimal extension temperatures, polymerase extension by the most commonly used thermostable polymerases (e.g., Taq polymerase and variants thereof) is performed at 65° C. to 75° C., preferably about 68–72° C.

As used herein, the term "aliquot" refers to a sample of an amplification reaction taken during the cycling regimen. An aliquot is less than the total volume of the reaction, and is preferably 0.1–30% in volume. In one embodiment of the invention, for each aliquot removed, an equal volume of reaction buffer containing reagents necessary for the reaction (e.g., buffer, salt, nucleotides, and polymerase enzyme) is introduced.

As used herein, the term "separating nucleic acid molecules" refers to the process of physically separating nucleic acid molecules in a sample or aliquot on the basis of size or charge. Electrophoretic separation is preferred, and capillary electrophoretic separation is most preferred.

As used herein, the term "real time" means that the measurement of the accumulation of products in a nucleic acid amplification reaction is at least initiated, and preferably completed during or concurrent with the amplification regimen. Thus, for the measurement process to be considered "real time", at least the initiation of the measurement or detection of amplification products in each aliquot is concurrent with the amplification process. By "initiated" is meant that an aliquot is withdrawn and placed into a separation apparatus, e.g., a capillary electrophoresis capillary, and separation is begun. The completion of the measurement is the detection of labeled species in the separated nucleic acids from the aliquot. Because the time necessary for separation and detection may exceed the time of each individual cycle of the amplification regimen, there may be a lag in the detection of the amplification products of up to 120 minutes beyond the completion of the amplification regimen. Preferably such lag or delay is less than 30 minutes, e.g., 25 minutes, 20 minutes, 15 minutes, 10 minutes, 5 minutes, 4 minutes, 3 minutes, 2 minutes, 1 minute or less, including no lag or delay.

As used herein, the term "capillary electrophoresis" means the electrophoretic separation of nucleic acid molecules in an aliquot from an amplification reaction wherein the separation is performed in a capillary tube. Capillary tubes are available with inner diameters from about 10 to 300 μm, and can range from about 0.2 cm to about 3 m in length, but are preferably in the range of 0.5 cm to 20 cm, more preferably in the range of 0.5 cm to 10 cm. In addition, the use of microfluidic microcapillaries (available, e.g., from Caliper or Agilent Technologies) is specifically contemplated within the meaning of "capillary electrophoresis."

As used herein, the term "reverse transcription reaction" refers to an in vitro enzymatic reaction in which the template-dependent polymerization of a DNA strand complementary to an RNA template occurs. Reverse transcription is performed by the extension of an oligonucleotide primer annealed to the RNA template, and most often uses a viral reverse-transcriptase enzyme, such as AMV (avian myeloblastosis virus) reverse transcriptase, or MMLV (Moloney murine leukemia virus) reverse transcriptase or thermostable DNA polymerase capable of using RNA as a template (e.g. Tfh DNA polymerase). Conditions and methods for reverse transcription are well known in the art. Exemplary conditions for reverse transcription include the following: for AMV reverse transcriptase—reaction at 37–55° C. in buffer containing 50 mM Tris-HCl, pH 8.3, 75 mM KCl, 3 mM $MgCl_2$, 10 mM DTT, 0.8 mM dNTPs, 50 units of reverse transcriptase, and 1–5 μg of template RNA and other additives (e.g BSA, glycerol, carbohydrates (glucose, trehalose); for MMLV reverse transcriptase—reaction at 37–55° C. in buffer containing 50 mM Tris-HCl, pH 8.3, 30 mM KCl, 8 mM $MgCl_2$, 10 mM DTT, 0.8 mM dNTPs, 50 units of reverse transcriptase, and 1–5 μg of template RNA and other additives (e.g BSA, glycerol, carbohydrates (glucose, trehalose).

As used herein, the term "modular apparatus" means an apparatus that comprises individual units in which certain processes of the methods according to the invention are performed. The individual units of a modular apparatus can be but are not necessarily physically connected, but it is preferred that the individual units are controlled by a central control device such as a computer. An example of a modular apparatus useful according to the invention has a thermal cycler unit, a sampler unit, and a capillary electrophoresis unit with a fluorescence detector. The modular apparatus useful according to the invention can also comprise a robotic arm to transfer samples from the cycling reaction to the electrophoresis unit.

As used herein, the term "sampling device" refers to a mechanism that withdraws an aliquot from an amplification during the amplification regimen. Sampling devices useful according to the invention will preferably be adapted to minimize contamination of the cycling reaction(s), by, for example, using pipeting tips or needles that are either disposed of after a single sample is withdrawn, or by incorporating one or more steps of washing the needle or tip after each sample is withdrawn. Alternatively, the sampling device can contact the capillary to be used for capillary electrophoresis directly with the amplification reaction in order to load an aliquot into the capillary. Alternatively, the sample device can include a fluidic line (e.g. a tube) connected to the controllable valve which will open at particular cycle. Sampling devices known in the art include, for example, the multipurpose Robbins Scientific Hydra 96 pipettor, which is adapted to sampling to or from 96 well plates. This and others can be readily adapted for use according to the methods of the invention.

As used herein, the term "robotic arm" means a device, preferably controlled by a microprocessor, that physically transfers samples, tubes, or plates containing samples from one location to another. Each location can be a unit in a modular apparatus useful according to the invention. An example of a robotic arm useful according to the invention is the Mitsubishi RV-E2 Robotic Arm. Software for the control of robotic arms is generally available from the manufacturer of the arm.

As used herein, the term "abundance of nucleic acid" refers to the amount of a particular target nucleic acid sequence present in a sample or aliquot. The amount is generally measured as a relative amount in terms of concentration or copy number of the target sequence relative to the amount of a standard of known concentration or copy number. Alternatively, the amount in one unknown sample is measured relative to the amount in another unknown sample. As used herein, abundance of a nucleic acid is measured on the basis of the intensity of a detectable label, most often a fluorescent label. The methods of the invention permit one to extrapolate the relative amount of one or more target sequences in a nucleic acid sample from the amplification profile of that target sequence or sequences from that sample.

As used herein, the term "amplified product" refers to polynucleotides which are copies of a portion of a particular polynucleotide sequence and/or its complementary sequence, which correspond in nucleotide sequence to the template polynucleotide sequence and its complementary sequence. An "amplified product," according to the invention, may be DNA or RNA, and it may be double-stranded or single-stranded.

As used herein, the term "distinctly sized amplification product" means an amplification product that is resolvable from amplification products of different sizes. "Different sizes" refers to nucleic acid molecules that differ by at least one nucleotide in length. Generally, distinctly sized amplification products useful according to the invention differ by greater than or equal to more nucleotides than the limit of resolution for the separation process used in a given method according to the invention. For example, when the limit of resolution of separation is one base, distinctly sized amplification products differ by at least one base in length, but can differ by 2 bases, 5 bases, 10 bases, 20 bases, 50 bases, 100 bases or more. When the limit of resolution is, for example, 10 bases, distinctly sized amplification products will differ by at least 10 bases, but can differ by 11 bases, 15 bases, 20 bases, 30 bases, 50 bases, 100 bases or more.

As used herein, the term "profile" or the equivalent terms "amplification curve" and "amplification plot" mean a mathematical curve representing the signal from a detectable label incorporated into a nucleic acid sequence of interest at two or more steps in an amplification regimen, plotted as a function of the cycle number from which the samples were withdrawn. The profile is preferably generated by plotting the fluorescence of each band detected after capillary electrophoresis separation of nucleic acids in the individual reaction samples. Most commercially available fluorescence detectors are interfaced with software permitting the generation of curves based on the signal detected.

As used herein, the term "first strand cDNAs" means the products of a reverse transcription reaction.

As used herein, the term "sample-specific sequence tag" refers to a polynucleotide sequence which is used to identify a polynucleotide molecule derived from a specific sample source. A "sample-specific sequence tag" of the present invention indicates the sample source of an isolated or synthesized polynucleotide and distinguishes an isolated or synthesized polynucleotide of one sample from that of another sample. Therefore, a sample-specific sequence tag has a specific sequence identity which can be identified. By "specific sequence identity" is meant that one sample-specific sequence should be different from another sample-specific sequence in at least one nucleotide, for example, in at least 2, or 3, or 4, or 5, or 10, or 15, or 20, or more, up to 60 nucleotides.

As used herein, the term "distinguishably labeled" means that the signal from one labeled oligonucleotide primer or a nucleic acid molecule into which it is incorporated can be distinguished from the signal from another such labeled primer or nucleic acid molecule. Detectable labels can comprise, for example, a light-absorbing dye, a fluorescent dye, or a radioactive label. Fluorescent dyes are preferred. Generally, a fluorescent signal is distinguishable from another fluorescent signal if the peak emission wavelengths are separated by at least 20 nm. Greater peak separation is preferred, especially where the emission peaks of fluorophores in a given reaction are wide, as opposed to narrow or more abrupt peaks.

As used herein, the term "set" means a group of nucleic acid samples, primers or other entities. A set will comprise a known number of, and at least two of such entities.

As used herein, the term "subset" means a group comprised by a set as defined herein, wherein the subset group is less than every member of the set. A subset as used herein can consist of a single entity, but is preferably more than one entity.

The number of genes that could be investigated in a single reaction can be estimated based on the measurable difference of the product size (1–2 bases) and on the separable size of PCR products (500–1000 bp) and can be as high as 1000, but preferably 100–200.

DETAILED DESCRIPTION OF THE INVENTION

Figure 1:
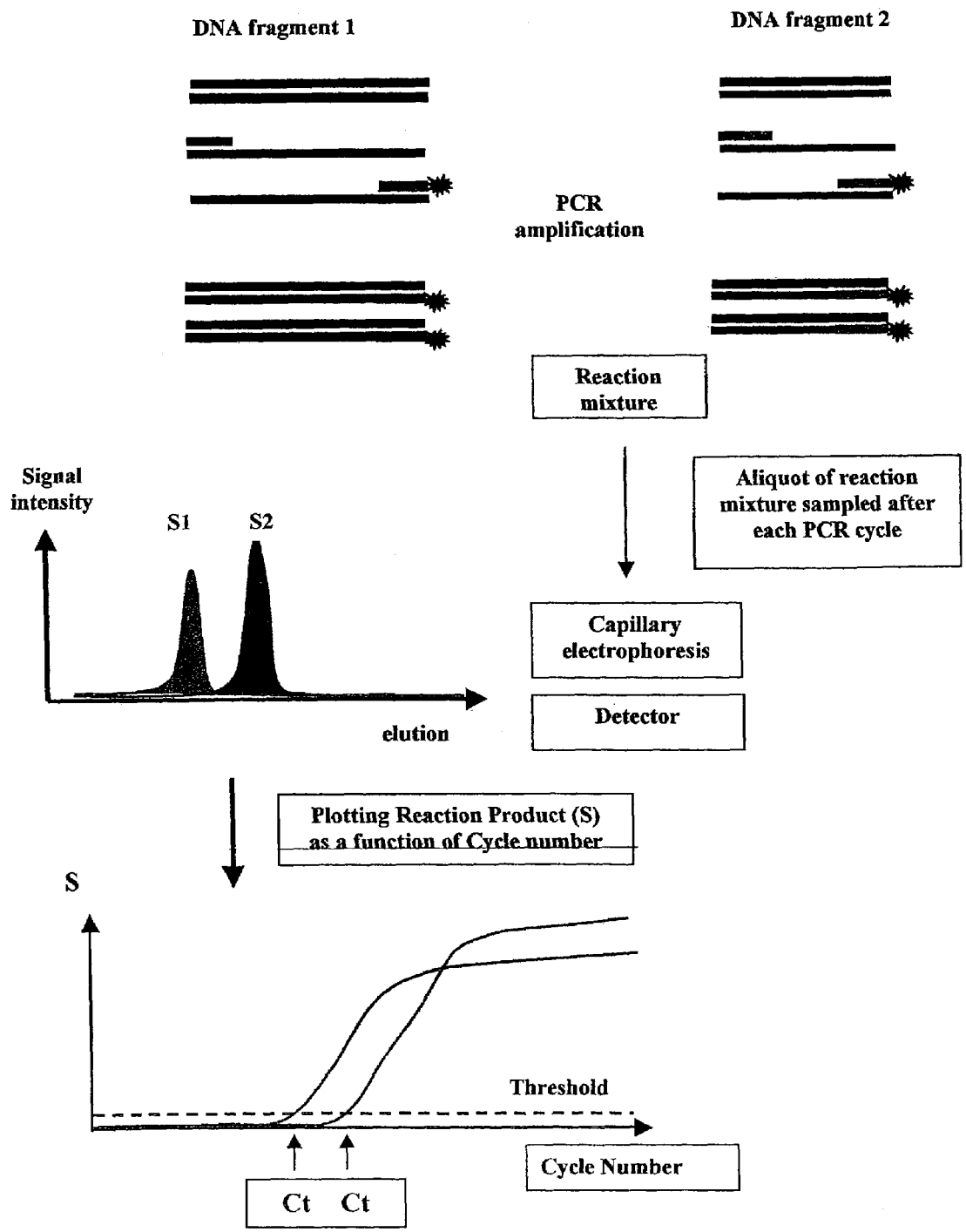
FIGS. 1–6 are diagrams schematically showing preferred embodiments of different aspects of the invention described in detail herein below.

The invention relates to methods for analyzing levels of gene expression, both in a single individual or sample and between two or more individuals or samples. The methods rely on the ability of the polymerase chain reaction (PCR) to quantitatively produce copies of one or more sequences of interest in a sample in a number sufficient to detect those copies above the background of other sequences present in the sample.

In PCR, two oligonucleotide primers, a template and a thermostable nucleic acid polymerase are used. In the general PCR scheme, one of the oligonucleotide primers anneals to a template nucleic acid strand. The annealed primer is extended by the thermostable template-dependent nucleic acid polymerase, and that polymerization product has a sequence complementary to the second primer such that the polymerization product can serve as template for the extension of the second primer. The polymerization product is thermally denatured to separate the strands, and the pair of primers is annealed to the respective strands and extended. Because each extension product serves as the template for subsequent extension reactions, the target sequence is exponentially amplified.

The amount of PCR product produced in a reaction can reflect the amount of template present in the original sample. While PCR is a powerful tool in the quantitative analysis of gene expression, it is known in the art that quantitative PCR requires careful and sometimes elaborate controls in order to ensure that the amount of product detected accurately reflects the amount of target RNA or DNA present in the original sample. Quantitative PCR is described, for example by Reischl & Kochanowski, 1995; Mol. Biotechnol. 3:55–71, and Jung et al, 2000, Clin. Chem. Lab. Med. 38:833–836.

PCR amplification is only quantitative during the exponential phase of the amplification. After the exponential phase gives way to a plateau, the amount of product detected does not accurately reflect the amount of target sequence present in the initial sample. The exhaustion of primer and nucleotide supplies, the accumulation of phosphate and the accumulation of amplified products themselves all contribute to non-linearity between the amount of input nucleic acid and the amount of output PCR product after the exponential phase of the amplification. In addition, when two or more distinct targets are amplified, differences in the efficiency of amplification of one product versus another will result in inaccuracy in the relative quantitation of target molecules present in the original sample. Thus, in order to obtain meaningful results from quantitative PCR methods, it is important to be able to monitor not only the amount of product generated, but how and when that product was generated.

The methods according to the invention overcome a number of the difficulties involved in quantitative PCR. For example, the methods provided herein permit the determination of the amount of amplification product made and simultaneously provide a curve showing the manner in which the product was made. The methods also permit the distinction between amplification signal arising from desired product and from artifacts, such as primer dimer formation or mispriming events.

In one aspect, the invention provides a method of monitoring the amplification of a single target nucleic acid from one sample. This and other aspects of the invention are suited for monitoring the amplification of polynucleotide sequences from samples containing DNA, RNA, or a mixture of these, but will most often find application in measuring or comparing RNA transcript levels in a sample. For the measurement of RNA transcripts, a reverse-transcription step is required. Reverse-transcription methods are well known in the art. Depending upon the desired assay, reverse-transcription can be performed using a non-specific primer (e.g., an oligo-dT-containing primer or a collection of random primers), or reverse-transcription can be performed using a primer specific for a gene of interest.

In this aspect, a nucleic acid sample is subjected to a PCR amplification regimen comprising at least two cycles of thermal denaturation, primer annealing and primer extension. The amplification regimen will preferably comprise 2 to 35 cycles, more preferably 10 to 30 cycles, more preferably 15 to 25 cycles. The regimen uses a pair of oligonucleotide primers that result in the specific amplification of a single sequence of interest if that sequence is present in the sample. One of the oligonucleotide primers is fluorescently labeled, such that each double-stranded amplification product will bear a detectable fluorescent marker.

During the cycling regimen, following at least one of the cycles of denaturation, primer annealing and primer extension in this aspect of the invention, a sample or aliquot of the reaction is withdrawn from the tube or reaction vessel, and nucleic acids in the aliquot are separated and detected. The separation and detection are performed concurrently with the cycling regimen, such that a curve representing product abundance as a function of cycle number is generated while the cycling occurs. As used herein, the term "concurrently" means that the separation is at least initiated while the cycling regimen is proceeding. Depending upon the separation technology used (e.g., capillary electrophoresis) and the number and size of species to be separated in a given reaction, the separation will most often require on the order of 1–120 minutes per aliquot. Thus, when separation steps take longer than the duration of each cycle, and when samples are withdrawn after, for example, every cycle, the separation steps will be completed after the completion of the full cycling regimen. However, as used herein, this situation is still considered to be "concurrent" separation, as long as the separation of each sample was initiated during the cycling regimen. Concurrent separation is most preferably performed through use of a robotic sampler that deposits the samples to the separation apparatus immediately after the samples are withdrawn from the cycling reaction.

In the manner described above, one can monitor the amplification reaction in real time, and the correlation between target product abundance and amount of target sequence in the original sample can be drawn more rapidly and more accurately than is achievable by other quantitative PCR methods. Aliquot removal (referred to herein as "sampling," nucleic acid separation, and detection can be performed as described herein below.

This method further extends the advantages offered by real-time PCR methods and also solves several commonly occurring problems inherent to these methods. At the beginning of the PCR amplification reaction, the amount of PCR product is below the detection limit of most instruments and no quantitative difference can be observed. For the detection of rare gene transcripts which are normally present at the level of several copies per cell, monitoring PCR products at very late stages will be necessary. Typically, detection of these genes will be difficult because the reaction is stopped before those rare transcripts are amplified to a detectable level. The middle section of the amplification curve, when the signal arises above the detection limit and enters a logarithmic phase, constitutes the best signal for detecting quantitative differences in gene expression. However, due to the exponential nature of the reaction, this phase is relatively short and lasts only a few cycles before the reaction goes into a later stationary phase. In this later stationary phase of PCR amplification, accumulation of PCR products are saturated due to factors such as lack of additional substrates, lack of polymerase, inhibition of polymerase activity by the product, or a combination thereof. The stationary phase provides little opportunity for detecting quantitative differences in gene expression. Therefore, methods that quantify PCR product after a predetermined number of cycles can only identify genes that happen to be in the logarithmic phase of the amplification and would thus miss those genes that are only differentially detected either earlier or later in the amplification process.

The instant invention overcomes this limitation because it defines a complete amplification curve for each individual amplified fragment. Moreover, it provides a quantitative basis for measuring expression differences. In the practice of real time quantitative PCR, the experimentally defined parameter "$C_t$," refers to the cycle number at which the signal generated from a quantitative PCR reaction first rises above a "threshold", i.e., where there is the first reliable detection of amplification of a target nucleic acid sequence. "Reliable" means that the signal reflects a detectable level of amplified product during PCR. $C_t$ generally correlates with starting quantity of an unknown amount of a target nucleic acid, i.e., lower amounts of target result in later $C_t$. $C_t$ is linked to the initial copy number or concentration of starting DNA by a simple mathematical equation:

Log(copy number)=$aC_t+b$, where $a$ and $b$ are constants.

Therefore, by measuring $C_t$ for the fragments of the same gene originating from two different samples, the original relative concentration of this gene in these samples can be easily evaluated.

One of the most interesting features of the PCR amplification is the ability to combine amplification of several target sequences in a single reaction which can provide a significant savings in time and cost of PCR assays. There are several methods are available that permit the co-amplification of multiple different polynucleotide sequences in a single amplification reaction. See e.g., Markoulatos et al. 2002, J. Clin. Lab. Anal. 16:47–51 and Broude et al., 2001, Antisense Nucleic Acid Drug Dev. 11:327–332. However, the majority of these methods do not provide quantitative data and are primarily used for the detection of the presence or absence of the particular sequences. Multiplex real-time applications are limited in the number of genes that could be combined in a single reaction by the optical separation of fluorescent dyes. In addition, these methods often cannot discriminate between specific and non-specific amplification products, further complicating quantitative analysis and requiring laborious assay optimization.

In another aspect, the invention eliminates the limits on the number of genes that can be analyzed in a single reaction. Specifically, the invention permits the monitoring of the amplification of more than one polynucleotide sequence in a sample. The method generates an amplification profile for two or more sequences that permits one to correlate signal strength during the logarithmic phase of the amplification to the relative amount of those sequences present in the original sample.

In this aspect of the invention, a set of oligonucleotide primers is used, and the set is comprised of pairs of oligonucleotide PCR primers specific for the two or more genes of interest. One primer of each pair of primers is fluorescently labeled with a fluorescent marker. An example of this aspect of the invention is depicted schematically in FIG. 1. In one embodiment, the different primers can be labeled with the same fluorescent marker. In that instance, the primers for the different amplification products are selected such that the sizes of the amplified products are distinct. As used in this context, "distinct" refers to a difference in sequence length that can be distinguished using the selected separation technology; amplified products differing by as little as a single nucleotide are distinct as long as the separation technology (e.g., capillary electrophoresis—see below) is capable of resolving that difference. PCR products useful according to the invention will generally be at least 50 bp in length, and can be as long as about 5,000 bp. Most often, PCR fragment lengths useful according to the invention will be on the order of 50–1000 bp in length, preferably 50–500 bp.

In another embodiment, one member of each pair of PCR primers is fluorescently labeled with a fluorophore that is spectrally distinguishable from the fluorophores labeling a member of each other pair of primers. In this embodiment, the sizes of the expected amplification products can be, but need not be distinct. It is assumed that spectrally distinguishable fluorophores used in a given reaction are selected such that they do not quench or engage in energy transfer with other fluorophores in the same reaction.

In an embodiment that further increases the capacity for simultaneous detection of different sequences in a single sample, the pairs of oligonucleotides are selected such that each pair generates either a distinctly sized fragment or is labeled with a distinct fluorophore or both. In this embodiment, different products that are the same size will have spectrally distinct fluorophores, and different products that are labeled with the same fluorophore will have distinct sizes.

In this aspect of the invention, once the desired combination of label and expected product sizes is selected, the nucleic acid sample is contacted with the set of pairs of primers, in a PCR reaction mixture comprising a nucleic acid polymerase, nucleotides and necessary buffer. The reaction mixture is then subjected to a PCR amplification regimen comprising iterative cycles of thermal denaturing, primer annealing, and primer extension. During this regimen, aliquots of the reaction are removed as described herein (see "Sampling" section, below) and the nucleic acids in the aliquot are separated as also described herein below. In this aspect of the invention, as in the others, the separation process is performed concurrently with the cycling reaction, and amplified nucleic acids are detected by the fluorescence of their markers.

The separation and detection steps permits the identification of amplified products by their size, fluorescent marker, or both, depending upon the combination of expected product sizes and spectrally distinguishable markers used. Thus, when the products bear the same marker, the separation will generate a "ladder" of fragments comprising the same label, and fragment size will distinguish one product from another. When the products bear different labels, the separation will generate bands comprising each different label that identify the amplified products. Finally, when the products are selected to be of distinct sizes and be distinctly labeled, the products are uniquely identified by the wavelength of fluorescence and the size of the fragment.

Aside from identifying the products, the detection step determines the abundance of each product present at each cycle sampled. This abundance can be plotted for each fragment to generate a fragment-specific amplification profile which can be used to extrapolate the relative abundance of the sequence represented by each detected fragment in the original sample.

Figure 2:
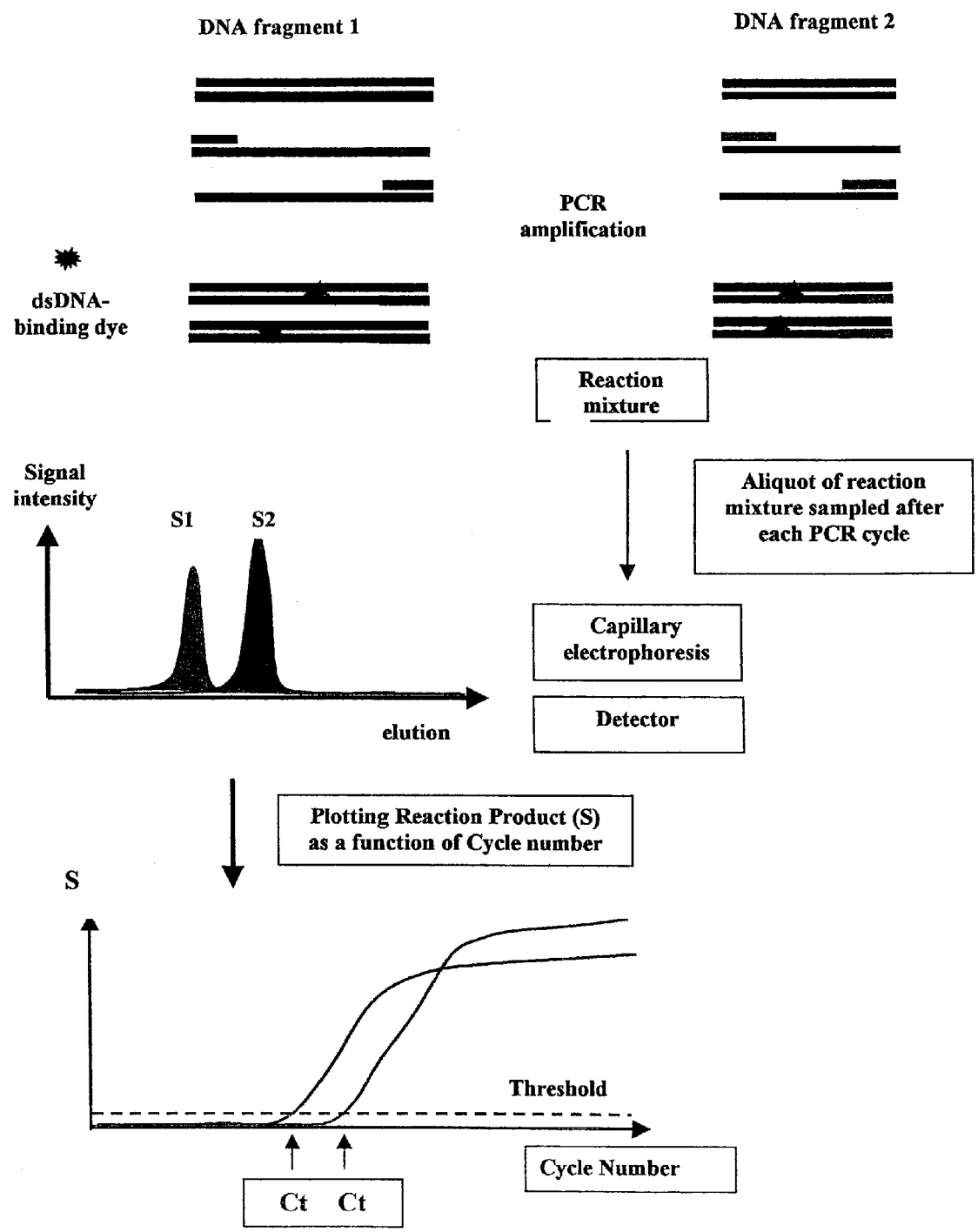

In another aspect of the invention, the amplification of a set of nucleic acid fragments present in a single sample can be monitored by using a set of pairs of forward and reverse oligonucleotide primers specific for each nucleic acid fragment of interest in the set of nucleic acid fragments. Primer pairs are selected so that the amplification product of each pair will be distinctly sized relative to other amplification products in the same reaction. PCR amplification is performed in the presence of a fluorescent dye (e.g., SYBR-Green; Molecular Probes Inc., Eugene, Oreg.) that binds only double-stranded DNA. During the amplification regimen, aliquots of the reaction are removed and the nucleic acids in the aliquot are separated as described herein. In this aspect of the invention, as in the others, the separation process is performed concurrently with the cycling reaction, and amplified double-stranded nucleic acids are detected by fluorescence and size. The abundance of each amplified fragment is identified by fluorescence intensity of the bound dye. The distinct sizes of the amplification products permit one to monitor the amplification of each nucleic acid fragment of interest throughout the amplification reaction, thereby generating an amplification curve for each nucleic acid fragment of interest. The curve indicates at which cycle each member of the set of nucleic acid fragments was in the logarithmic phase of amplification, thereby permitting extrapolation of the relative abundance of each member of the set in the original sample. This aspect of the invention is depicted schematically in FIG. 2.

In another aspect, the invention provides an alternative method of monitoring the amplification of a set of polynucleotide sequences present in a single sample. In this method, RNAs in a sample are reverse transcribed using a primer that comprises, at the 5' end, a tag sequence of 10–40 nucleotides and sequence complimentary to mRNA that can be of the specific gene target or can represent an oligo-dT stretch (which stretch is generally 8–30 nucleotides long, preferably 12–24 nucleotides). The tag sequence should be a sequence that is not represented in the genome of the organism being investigated, and can be synthetic, random or derived from another species. The tag sequence should be long enough to provide specific annealing with a polynucleotide comprising a complementary sequence under the salt and annealing temperature conditions of a given PCR reaction. These conditions, particularly annealing temperature, vary, but such temperature is determined on the basis of the known or predicted $T_m$ of the tag sequence. Commercial programs, including Oligo™, Primer Design and programs available on the internet, including Primer3 and Oligo Calculator can be used to predict the $T_m$ of a polynucleotide sequence useful according to the invention. The tag sequence useful in this and other aspects of the invention should be selected to have a $T_m$ in the range of 50°–60° C.

Reverse-transcription of RNAs in a sample using the primer described above (e.g. oligo-dT-Tag primer or mRNA complement-Tag primer) will result in a population of reverse-transcription products that each bears the tag sequence 5' of the sequence complimentary to mRNA (e.g. oligo-dT stretch or mRNA complement stretch). In order to amplify a set of polynucleotide sequences represented in the reverse-transcribed sample, the reverse-transcription reaction or an aliquot of it is mixed with with (i) a set of oligonucleotide primers that recognize or specifically hybridize to the set of nucleic acid sequences of interest, and (ii) a detectably labeled oligonucleotide primer that comprises the sequence tag common to all of the reverse-transcription products. In this aspect of the invention, each oligonucleotide primer specific for a member of the set of transcripts of interest is selected so that it generates a distinctly sized amplification product in the subsequent amplification regimen.

The mixture of primers and reverse transcription products is then subjected to an amplification regimen as in the previous aspects of the invention. Each amplification product will be a distinct size from the other expected fragments, and each amplification product will also comprise a detectable label, preferably a fluorophore, such that the fragments can be readily detected after separation.

Figure 3:
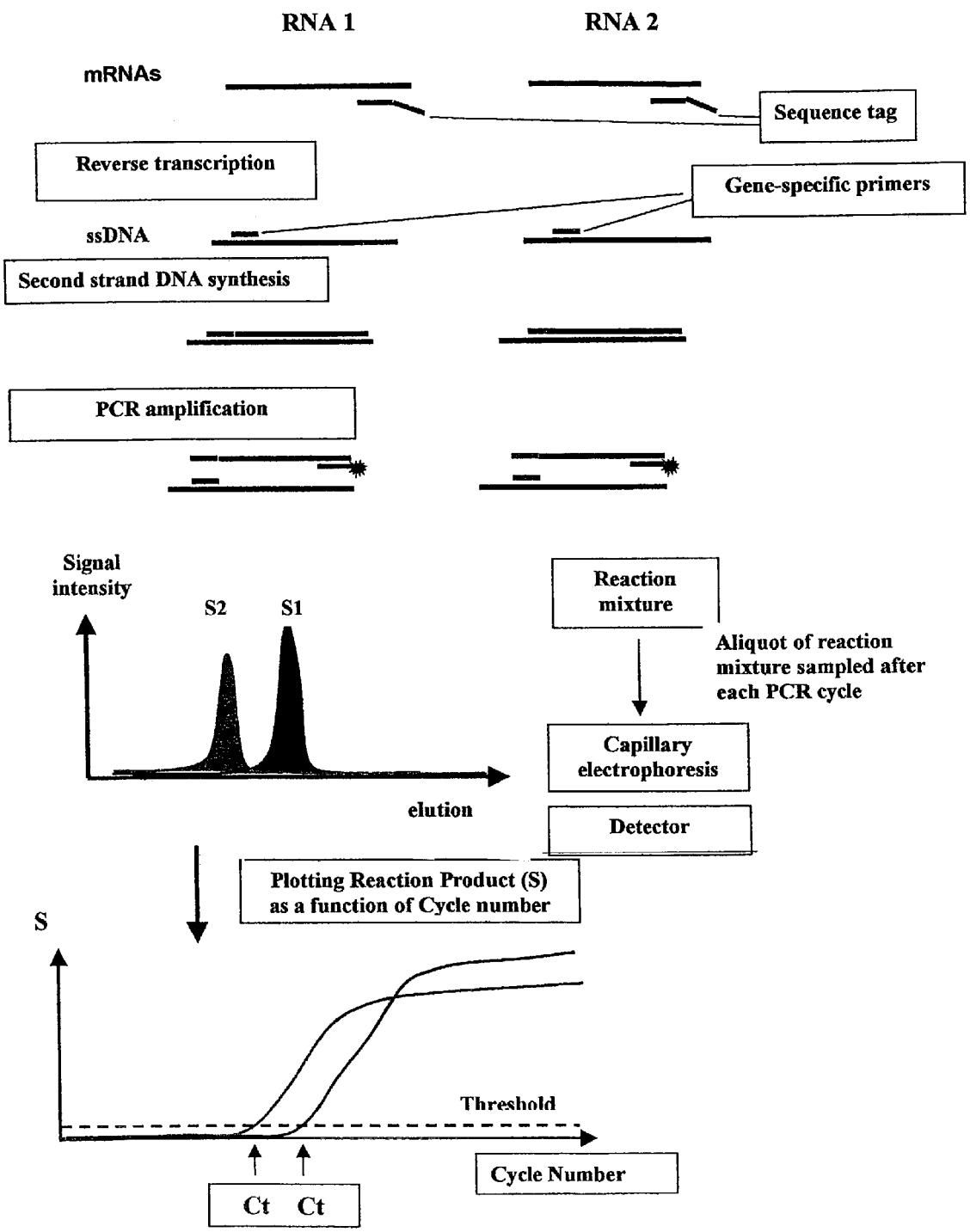

As in other aspects of the invention, samples of the amplification reaction are taken during the cycling regimen and the amplification products are separated and detected. The identities of the amplification products are determined by their size, and the abundance of each amplification product at each cycle is determined by the intensity of label in the product of the expected size. The amplification curve generated by the sampling and separation provides a profile for the amplification of each member of the set. This profile indicates at which cycle each member of the set of transcripts or genes of interest was in the logarithmic phase of amplification, thereby permitting extrapolation of the relative abundance of each member of the set in the original sample. This aspect of the invention is depicted schematically in FIG. 3.

In another aspect, the invention provides a method for comparing the expression of a nucleic acid sequence of interest between a two samples. RNAs in a sample are reverse transcribed using a primer that comprises, at its 5' end, a tag sequence of 15–40 nucleotides and sequence complimentary to mRNA that can be gene specific or can represent an oligo-dT stretch (which stretch is generally 8–30 nucleotides long, preferably 12–24 nucleotides). Reverse-transcription of each sample will result in a population of reverse-transcription products each bearing a sample-specific sequence tag. Sample-specific tags are unique sequences of 8–30 nucleotides in length, preferably 12–24 nucleotides in length, that specifically hybridize or anneal to a complementary sequence under salt and temperature conditions for PCR annealing reactions as described above.

Following separate reverse-transcription reactions, the synthesis of the complimentary DNA strand is initiated with primers that contain at their 5' ends a unique sequence tag (tag 2) of 8–40 nucleotides followed by gene-specific sequence (8–30 nucleotides). Following the primer extension with DNA polymerase, the unreacted primers are eliminated by heat-sensitive nuclease which is then destroyed by incubation at increased temperature. In this aspect of the invention, each oligonucleotide primer used for priming of the complimentary DNA strand specific for a member of the set of transcripts of interest is selected so that it generates a distinctly sized amplification product in the subsequent amplification regimen.

In order to amplify a set of polynucleotide sequences represented in the synthesized DNA sample, the reaction or an aliquot of it is mixed with (i) oligonucleotide primer that comprises the specific sequence tag2, and (ii) a detectably labeled oligonucleotide primer that comprises the sequence tag common to all of the reverse-transcription products. The use of only 2 primers for amplification of the set of selected sequences will decrease the complexity of PCR amplification and improve the amplification yield.

Figure 4:
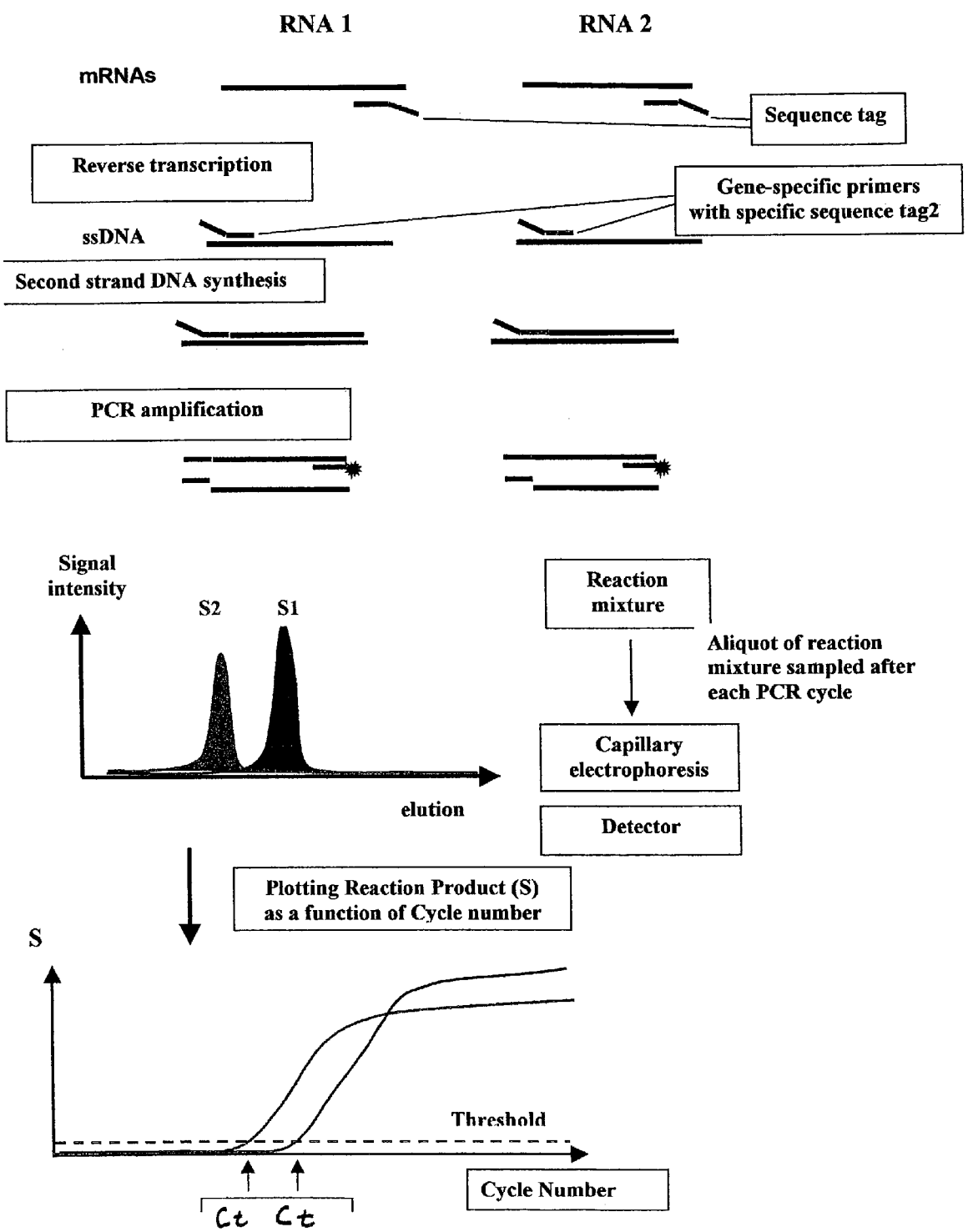
Figure 6:
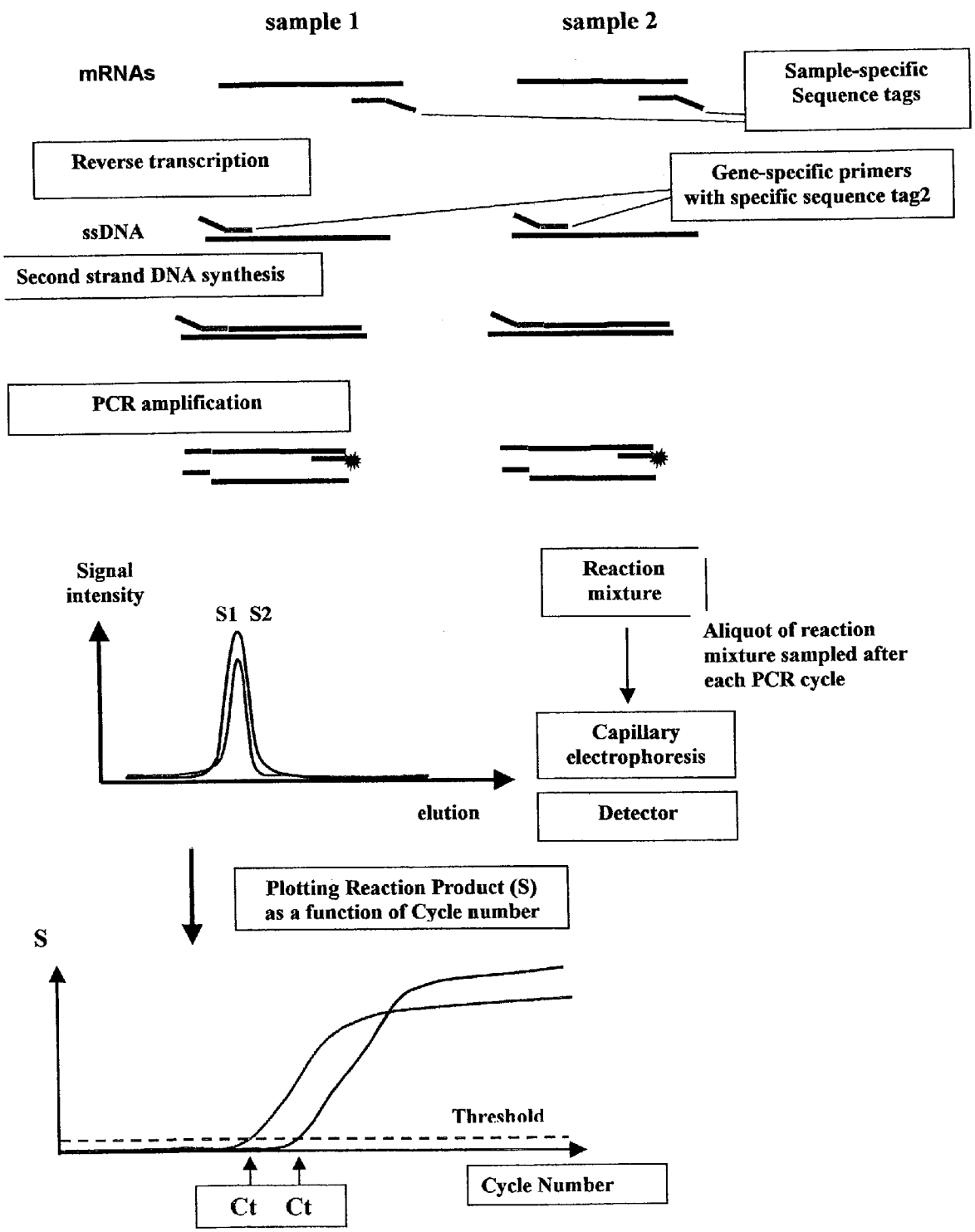

As in other aspects of the invention, samples of the amplification reaction are taken during the cycling regimen and the amplification products are separated and detected. The identities of the amplification products are determined by their size, and the abundance of each amplification product at each cycle is determined by the intensity of label in the product of the expected size. The amplification curve generated by the sampling and separation provides a profile for the amplification of each member of the set. This profile indicates at which cycle each member of the set of transcripts or genes of interest was in the logarithmic phase of amplification, thereby permitting extrapolation of the relative abundance of each member of the set in the original sample. Examples of this aspect of the invention are schematically depicted in FIGS. 4 and 6. In FIG. 4, amplification products of different size are detected with the same fluorescent label. In the alternative FIG. 6, amplification products of the same size are distinguished by distinguishable fluorescent labels on the sample-specific Tag primers.

Figure 5:
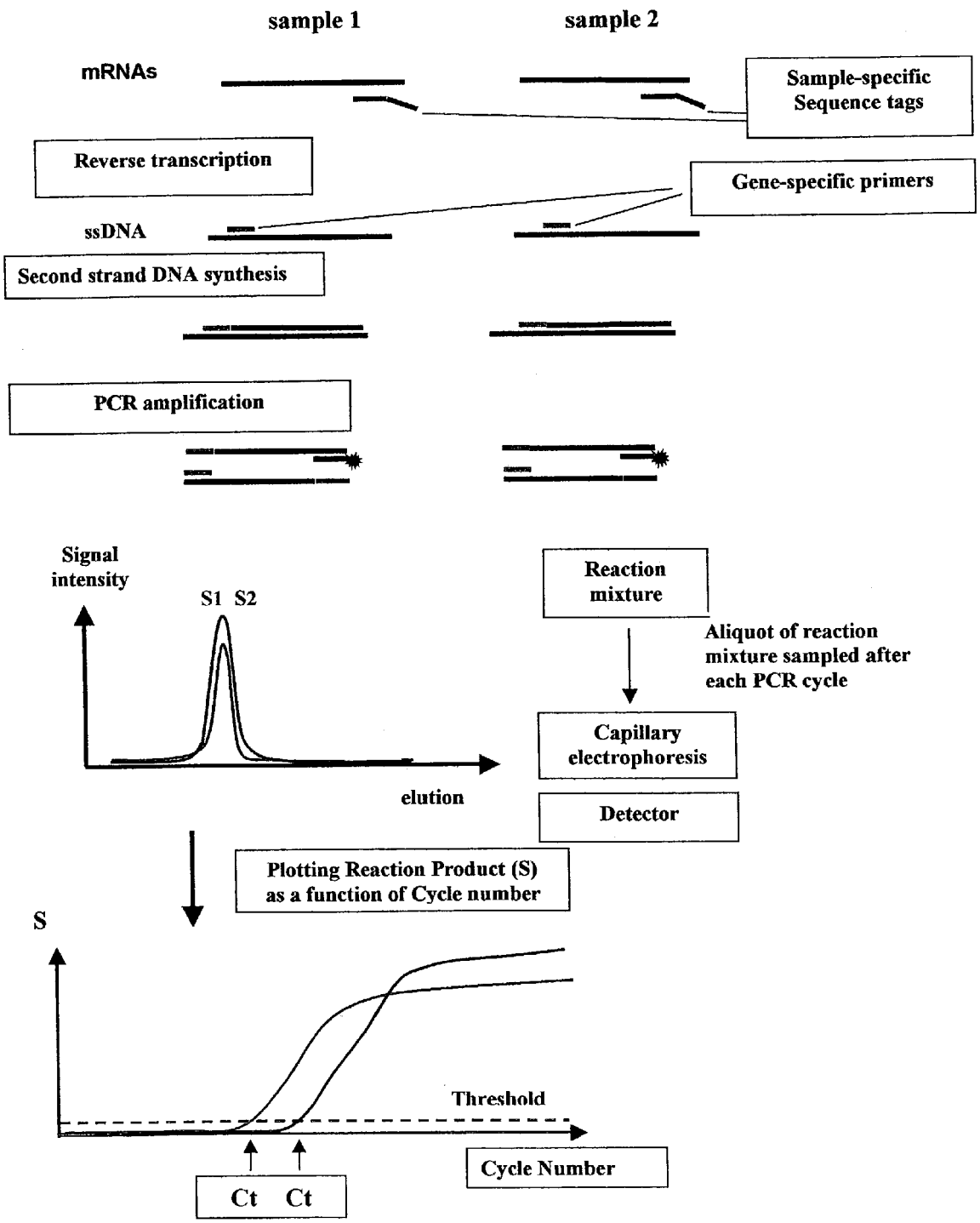

In another aspect, an example of which is depicted schematically in FIG. 5, the invention provides a method for comparing the expression of a nucleic acid sequence of interest between a two samples. RNAs in a sample are reverse transcribed using a primer that comprises, at its 5' end a tag sequence of 8–30 nucleotides and sequence complimentary to mRNA that can be gene specific or can represent an oligo-dT stretch (which stretch is generally 8–30 nucleotides long, preferably 12–24 nucleotides). Thus, reverse-transcription of each sample will result in a population of reverse-transcription products each bearing a sample-specific sequence tag. Sample-specific tags are unique sequences of 8–30 nucleotides in length, preferably 12–24 nucleotides in length, that specifically hybridize or anneal to a complementary sequence under salt and temperature conditions for PCR annealing reactions as described above.

Following separate reverse-transcription reactions, one for each sample being compared, equal amounts of the reverse-transcription reactions are mixed and the mixture is used as template in a PCR amplification regimen. For this amplification regimen, primers are used as follows: (i) a separate, distinguishably fluorescently labeled oligonucleotide primer corresponding to each sample-specific sequence tag used in the reverse transcription step—the sample-specific sequence should be long enough to permit specific annealing of the primer to a nucleic acid molecule comprising sequence complementary to the sample-specific tag when under temperature and salt conditions that permit such annealing (see discussion of $T_m$ prediction above); and (ii) an oligonucleotide primer specific for the sequence of interest (i.e., comprising sufficient sequence complementary to the nucleic acid sequence of interest to permit specific annealing of the primer to a nucleic acid molecule comprising the sequence of interest under conditions that permit that annealing, as described herein). The primer specific for the gene or transcript of interest will generally be selected such that a product of 50–5,000 bp is generated upon amplification, preferably 50–1000, more preferably 50–500 bp.

During the cycling regimen, samples are withdrawn from the amplification reaction, and amplified nucleic acids are separated and detected as in other aspects of the invention described herein. Because the separation and detection process detects the distinguishable labels attached to the primers specific for each sample of origin, this process generates a separate amplification profile for the gene of interest from each sample. Because there is competition for the gene- or transcript-specific primer (that is, the "upstream" primer), the effects of amplification bias are lessened, and the amplification profiles can be used to extrapolate the relative abundance of the gene of interest in the different original samples or to provide a relative abundance in comparison with a known standard.

In another aspect, the invention provides a method for monitoring the amplification of a set of nucleic acid sequences. In this method, a set of nucleic acid sequences present in a set of reverse-transcription products is amplified in a PCR amplification regimen involving at least two iterative cycles of thermal denaturing, primer annealing and polymerase extension.

The set of reverse transcription products is made up of subsets of reverse-transcription products, where each subset is the reverse-transcript population generated from one RNA sample. Each subset is made by reverse-transcribing a sample of RNA using a primer that comprises, at its 5' end a tag sequence of 15–40 nucleotides and sequence complimentary to mRNA that can be gene specific or can represent an oligo-dT stretch (which stretch is generally 8–30 nucleotides long, preferably 12–24 nucleotides). Equal amounts of the reverse-transcript subsets are then mixed to form the set of reverse-transcription products used as an amplification template for the subsequent amplification regimen.

The PCR amplification regimen for this aspect is performed by contacting the template comprising the mixed set of reverse-transcription products with two sets of amplification primers as follows: (i) a set of gene-specific primers, wherein each gene specific primer in the set recognizes or specifically hybridizes to a specific nucleic acid sequence of interest (i.e., a sequence expressed or thought to be expressed) in a nucleic acid sample—each gene specific primer in the set is selected so as to generate an amplification product that is distinct in size from amplification products generated with other gene specific primers in that set; and (ii) a set of sample specific primers. Each sample specific primer is selected such that it specifically hybridizes to the sample specific tag incorporated into the reverse-transcription products from one sample under PCR annealing conditions as described herein. Each sample specific primer in the set of sample specific primers is also distinguishably labeled.

During the cycling of the amplification regimen, samples are withdrawn and nucleic acids are separated and detected as for the other aspects of the invention described herein above. The detection provides a profile of the abundance of each distinctly-sized fragment representing a transcript of interest, and the distinguishable labels on the sample-specific probes permit one to distinguish signal arising from the individual samples. Thus, the method permits one to compare the relative abundance of a set of genes among a set of different samples. This method is particularly useful for monitoring the effect of a treatment, e.g., a drug treatment, on a group of related or unrelated genes in a cell type or tissue.

Because the separation and detection of the amplification products is performed concurrently with the cycling regimen, and because separation by, for example, CE, is very fast, the methods described herein permit the real time generation of amplification profiles that are useful for determining the relative abundance of nucleic acid species in the samples investigated.

A) Sampling

Sampling during the amplification regimen can be performed at any frequency or in any pattern desired. It is preferred that sampling occurs after each cycle in the regimen, although less frequent sampling can also be used, for example, every other cycle, every third cycle, every fourth cycle, etc. While a uniform sample interval will most often be desired, there is no requirement that sampling be performed at uniform intervals. As just one example, the sampling routine may involve sampling after every cycle for the first five cycles, and then sampling after every other cycle.

Sampling can be as simple as manually pipetting an aliquot from the reaction, but is preferably automated such that the aliquot is withdrawn robotically at predetermined sampling intervals. For this and other aspects of the invention, it is preferred, although not necessary that the cycling be performed in a microtiter or multiwell plate format. This format, which uses plates comprising multiple reaction wells, not only increases the throughput of the assay process, but is also well adapted for automated sampling steps due to the modular nature of the plates and the uniform grid layout of the wells on the plates. Common microtiter plate designs useful according to the invention have, for example 12, 24, 48, 96, 384 or more wells, although any number of wells that physically fit on the plate and accommodate the desired reaction volume (usually 10–100 μl) can be used according to the invention. Generally, the 96 or 384 well plate format is preferred.

An automated sampling process can be readily executed as a programmed routine and avoids both human error in sampling (i.e., error in sample size and tracking of sample identity) and the possibility of contamination from the person sampling. Robotic samplers capable of withdrawing aliquots from thermal cyclers are available in the art. For example, the Mitsubishi RV-E2 Robotic Arm can be used in conjunction with a SciClone™ Liquid Handler or a Robbins Scientific Hydra 96 pipettor.

The robotic sampler useful according to the invention can be integrated with the thermal cycler, or the sampler and cycler can be modular in design. When the cycler and sampler are integrated, thermal cycling and sampling occur in the same location, with samples being withdrawn at programmed intervals by a robotic sampler. When the cycler and sampler are modular in design, the cycler and sampler are separate modules. In one embodiment, the assay plate is physically moved, e.g., by a robotic arm, from the cycler to the sampler and back to the cycler.

The volume of an aliquot removed at the sampling step can vary, depending, for example, upon the total volume of the amplification reaction, the sensitivity of product detection, and the type of separation used. Amplification volumes can vary from several microliters to several hundred microliters (e.g., 5 μl, 10 μl, 20 μl, 40 μl, 60 μl, 80 μl, 100 μl, 120 μl, 150 μl, or 200 μl or more), preferably in the range of 10–150 μl, more preferably in the range of 10–100 μl. Aliquot volumes can vary from 0.1 to 30% of the reaction mixture.

B) Separation of Nucleic Acids

Separation of nucleic acids according to the invention can be achieved by any means suitable for separation of nucleic acids, including, for example, electrophoresis, HPLC or mass spectrometry. Separation is preferably performed by capillary electrophoresis (CE).

CE is an efficient analytical separation technique for the analysis of minute amounts of sample. CE separations are performed in a narrow diameter capillary tube, which is filled with an electrically conductive medium termed the "carrier electrolyte." An electric field is applied between the two ends of the capillary tube, and species in the sample move from one electrode toward the other electrode at a rate which is dependent on the electrophoretic mobility of each species, as well as on the rate of fluid movement in the tube. CE may be performed using gels or liquids, such as buffers, in the capillary. In one liquid mode, known as "free zone electrophoresis," separations are based on differences in the free solution mobility of sample species. In another liquid mode, micelles are used to effect separations based on differences in hydrophobicity. This is known as Micellar Electrokinetic Capillary Chromatography (MECC).

CE separates nucleic acid molecules on the basis of charge, which effectively results in their separation by size or number of nucleotides. When a number of fragments are produced, they will pass the fluorescence detector near the end of the capillary in ascending order of size. That is, smaller fragments will migrate ahead of larger ones and be detected first.

CE offers significant advantages of over conventional electrophoresis, primarily in the speed of separation, small size of the required sample (on the order of 1–50 nl), and high resolution. For example, separation speeds using CE can be 10 to 20 times faster than conventional gel electrophoresis, and no post-run staining is necessary. CE provides high resolution, separating molecules in the range of about 10–1,000 base pairs differing by as little as a single base pair. High resolution is possible in part because the large surface area of the capillary efficiently dissipates heat, permitting the use of high voltages. In addition, band broadening is minimized due to the narrow inner diameter of the capillary. In free-zone electrophoresis, the phenomenon of electroosmosis, or electroosmotic flow (EOF) occurs. This is a bulk flow of liquid that affects all of the sample molecules regardless of charge. Under certain conditions EOF can contribute to improved resolution and separation speed in free-zone CE.

CE can be performed by methods well known in the art, for example, as disclosed in U.S. Pat. Nos. 6,217,731; 6,001,230; and 5,963,456, which are incorporated herein by reference. High throughput CE equipment is available commercially, for example, the HTS9610 High Throughput Analysis System and SCE 9610 fully automated 96-capillary electrophoresis genetic analysis system from Spectrumedix Corporation (State College, Pa.). Others include the P/ACE 5000 series from Beckman Instruments Inc (Fullerton, Calif.) and the ABI PRISM 3100 genetic analyzer (Applied Biosystems, Foster City, Calif.). Each of these devices comprises a fluorescence detector that monitors the emission of light by molecules in the sample near the end of the CE column. The standard fluorescence detectors can distinguish numerous different wavelengths of fluorescence emission, providing the ability to detect multiple fluorescently labeled species in a single CE run from an amplification sample.

Another means of increasing the throughput of the CE separation is to use a plurality of capillaries, or preferably an array of capillaries. Capillary Array Electrophoresis (CAE) devices have been developed with 96 capillary capacity (e.g., the MegaBACE instrument from Molecular Dynamics) and higher, up to and including even 1000 capillaries. In order to avoid problems with the detection of fluorescence from DNA caused by light scattering between the closely juxtaposed multiple capillaries, a confocal fluorescence scanner can be used (Quesada et al., 1991, Biotechniques 10:616–25).

The apparatus for separation (and detection) can be separate from or integrated with the apparatus used for thermal cycling and sampling. Because according to the invention the separation step is initiated concurrently with the cycling regimen, samples are preferably taken directly from the amplification reaction and placed into the separation apparatus so that separation proceeds concurrently with amplification. Thus, while it is not necessary, it is preferred that the separation apparatus is integral with the thermal cycling and sampling apparatus. In one embodiment, this apparatus is modular, comprising a thermal cycling module and a separation/detection module, with a robotic sampler that withdraws sample from the thermal cycling reaction and places it into the separation/detection apparatus.

C) Detection

Amplification product detection methods useful according to the invention measure the intensity of fluorescence emitted by labeled primers when they are irradiated with light within the excitation spectrum of the fluorescent label. Fluorescence detection technology is highly developed and very sensitive, with documented detection down to a single molecule in some instances. High sensitivity fluorescence detection is a standard aspect of most commercially-available plate readers, microarray detection set-ups and CE apparatuses. For CE equipment, fiber optic transmission of excitation and emission signals is often employed. Spectrumedix, Applied Biosystems, Beckman Coulter and Agilent each sell CE equipment with fluorescence detectors sufficient for the fluorescence detection necessary for the methods described herein.

The fluorescence signals from two or more different fluorescent labels can be distinguished from each other if the peak wavelengths of emission are each separated by 20 nm or more in the spectrum. Generally the practitioner will select fluorophores with greater separation between peak wavelengths, particularly where the selected fluorophores have broad emission wavelength peaks. It follows that the more different fluorophores one wishes to include and detect concurrently in a sample, the narrower should be their emission peaks.

D) Fluorescent Markers

Numerous fluorescent markers useful according to the invention are commercially available. For example, Molecular Probes, Inc. (Eugene, Oreg.) sells a wide variety of fluorescent dyes. Non-limiting examples include Cy5, Cy3, TAMRA, R6G, R110, ROX, JOE, FAM, Texas Red™, and Oregon Green™, just to name a few. Fluorescent dyes useful according tot he invention can be attached to oligonucleotide primers using methods well known in the art. For example, one common way to add a fluorescent label to an oligonucleotide is to react an N-Hydroxysuccinimide (NHS) ester of the dye with a reactive amino group on the target. Nucleotides can be modified to carry a reactive amino group by, for example, inclusion of an allyl amine group on the nucleobase. Labeling via allyl amine is described, for example, in U.S. Pat. Nos. 5,476,928 and 5,958,691, which are incorporated herein by reference. Other means of fluorescently labeling nucleotides, oligonucleotides and polynucleotides are well known to those of skill in the art.

E) Correlation Between Fluorescence Signal from Amplified DNA and Nucleic Acid Levels Present in the Original Sample.

One source of concern regarding the use of PCR amplification for expression profiling is a potential bias of amplification. Some sequences are amplified with higher efficiency than others. This bias can change the final representation of PCR products when compared with the starting sample. Further, because of difficulties in determining the efficiency of RNA extraction and the efficiency of amplification, quantitative PCR is most readily used to examine relative differences in gene expression between two samples, rather than to measure the absolute amount of a target RNA in a given sample. The detected fluorescent signal strength (e.g., following CE separation) can be recorded and used to determine the relative ratio of each peak from a target sequence in two sample.

In a preferred embodiment, cDNAs derived from two or more samples are amplified in the same PCR reaction. Each target cDNA molecule is amplified by a common primer and a sample specific primer, such that cDNAs from different samples will compete for the same common primer. Because of this competition, the ratio of the amounts of the amplified products from two samples reflects the ratio of the amounts of the initial target polynucleotide in each of the two samples. A ratio of 1 for the amount of signal from sample A to that from sample B indicates the same initial amount of the target polynucleotide in the samples, i.e., the target polynucleotide is not differentially expressed in the two samples. An A/B ratio of greater than 1 indicates a higher amount of the target polynucleotide in sample A than in sample B. An A/B ratio of less than 1 indicates a lesser amount of the target polynucleotide in sample A than in sample B. When the ratio is greater than or less than 1, the target polynucleotide is differentially expressed in the two samples. It is expected that the levels of many polynucleotides present in two samples from the same species of organism will be approximately similar, resulting in a ratio near 1 for most gene products compared between two samples from either the same or different members of a single species. In practice according to the invention, a polynucleotide with a ratio greater than 2 or less than 0.5 relative to signal for the same gene from a different sample is regarded as a differentially expressed polynucleotide in the two samples.

The differences in expression between two samples from different tissues from one individual or between samples from two individuals of the same species are most likely limited to relatively few genes. Thus, the power of the methods of comparison described herein lies in their ability to resolve differences in the few individual genes from among a background of similar expression in most genes.

The similarity of the expression of the majority of genes between tissues or between individuals of the same species can also be used to advantage. The ratio of a particular polynucleotide in two samples can be further measured against a common ratio in order to determine whether it is differentially expressed between the two samples. The term "common ratio" as used herein means a relatively constant ratio of all genes expressed between two samples. Changes in the common ratio reflect a global change in the amount of total starting material, rather than a specific change caused by certain events such as activation of a particular signal transduction pathway in a treated sample as compared to an untreated sample. By comparing the ratio of expression of a particular gene with this common ratio, it will be immediately apparent whether the expression of that particular gene is different between the samples being compared.

If the two samples are amplified in separate PCR reactions, an internal control can be provided for each PCR amplification and the amplification of each sample is first normalized to the internal control before the ratio is calculated. The use of internal controls for quantitative PCR is well-known in the art, for example, as described in Ausubel et al. There are two basic types of control: the first is commonly known as an exogenous control (Gilliland et al. (1990) PCR Protocols, Innis et al. ed., pp. 60–69, Academic Press; Wang et al. (1989) Proc. Natl. Acad. Sci. USA 86:9717–9721, both of which are specifically incorporated herein by reference), and the second, is known as an endogenous control (Dveksler et al. (1992) PCR Methods and Applications 6:283–285; Spanakis (1993) Nucleic Acids Research 21:3809–3819, both of which are specifically incorporated herein by reference).

Exogenous controls involve the use of an artificially introduced nucleic acid molecule that is added, either to the extraction step or to the PCR step, in a known concentration. The concept of adding an exogenous nucleic acid at a known concentration in order to act as an internal standard for quantitation was introduced by Chelly et al. (1988) Nature 333:858–860, which is specifically incorporated herein by reference. The use of a control fragment that is amplified with the same primers as the target sequence more accurately reflects target sequence amplification efficiency relative to the internal standard (see, for example, WO 93/02215; WO 92/11273.; U.S. Pat. Nos. 5,213,961 and 5,219,727, all of which are incorporated herein by reference). Similar strategies have proven effective for quantitative measurement of nucleic acids utilizing isothermal amplification reactions such as NASBA (Kievits et al., 1991, J Virol Methods. 35:273–86) or SDA (Walker, 1994, Nucleic Acids Res. 22:2670–7).

The use of an endogenous control can compensate for variations in extraction efficiency. Choice of controls is important in that several requirements must be met in order for it to work. The first requirement is that the copy number of the control must remain constant. The second requirement is that the control must amplify with similar efficiency to the sequence being monitored. Several constitutively expressed genes have been considered as control candidates, because the expression of these genes is relatively constant over a variety of conditions. Examples include, but are not limited to, the β-actin gene, the glyceraldehyde-3-phosphate dehydrogenase gene (GAPDH), and the 16S ribosomal RNA gene.

EXAMPLES

Example 1

Quantitative Detection of Multiple Amplicons in a Single Amplification Reaction

Sample DNA constructs: DNA fragments cloned in pcDNA3 vector (Invitrogen) were amplified in PCR reaction using forward primer (5'-ATCGAAATTAATACGACTCACTAT-3'; SEQ ID NO: 1) and reverse primer (5'-AGCTCTAG-CATTTAGGTGACACTA-3'; SEQ ID NO: 2). Amplified DNA fragments were purified by agarose gel electrophoresis and extracted from the gel using a purification kit (Qiagen). Corresponding RNA fragments containing unique sequence tags were prepared using T7 RNA polymerase transcription kit (Invitrogen) and purified by "RNA Easy" RNA purification kit (Qiagen). Concentration of RNA fragments was measured on SmartSpec 3000 spectrophotometer (Bio-Rad).

Preparation of oligonucleotides covalently coupled to solid support: Oligonucleotides TJLF (5'-AATTCCGCGC-CGAATAATATTAAGCTCTAGCATTTAG-3'; SEQ ID NO: 3) and (5'-AATTCCCGGCGGATTATTTATT-AGCTCTAGCATTTAG-3'; SEQ ID NO: 4) containing sequence tags LFAM 2(5'-CCGCGCCGAATAATATTAA-3'; SEQ ID NO: 5) and LROX (5'-CCCGGCGGATT ATT-TATTA-3'; SEQ ID NO: 6) and 5'thiol modification were coupled to polymer beads containing iodoacetyl groups. Oligonucleotides (12.5 uM) were incubated with 200 ul of Thiolink beads (Pierce) pre-washed with 5×TE buffer (50 mM Tris, 5 mM EDTA, pH 8.0) and 200 uM TCEP (Molecular probes) for 1 hour at room temperature under constant mixing. Unreacted iodoacetyl groups were quenched by incubation with 1% beta-mercaptoethanol at room temperature. Beads were washed 4 times with 5×TE buffer, 2 times 5×TE at 75° C., 1 wash with RT (reverse transcription) buffer at room temperature and 2 washes with RT buffer at 95 C (all washes with 1 ml of buffer). Prepared beads were made as 50% suspension in RT buffer.

Reverse transcription reaction: 10 ul of modified beads (TJLF or TJLR1) were combined with 1 ul of dNTP (10 mM), 1 ul of sample RNAs (VS31 (53 pg) and VS67 (1.1 pg), TJLF beads, VS68(0.058 pg) and VS67(0.094 pg), TJLR1 beads) heated for 5 min at 70° C., cooled at 4° C. and supplemented with 10 ul of the reaction mix (1 ul of Superscript reverse transcriptase (Invitrogen) diluted 4 times, 2 ul of 0.1 M DTT, 4 ul of 5× reaction buffer (Invitrogen), 10 ul of water). The reaction mixture was incubated for 1 hour at 42° C., 10 min at 65° C. RNA was hydrolyzed by addition of 3.5 ul of 0.5M NaOH and heating 5 min at 65° C. followed by addition of 3.5 ul of 1 M Tris, pH 7.5. Beads were washed with 100 ul of PCR buffer.

$2^{nd}$ strand synthesis: 100 ul of the reaction mixture containing 10 ul of PCR buffer (for Pwo DNA polymerase, (Roche)), 2 ml of 25 mM $MgCl_2$, 2 ul of 10 mM dNTPs, 0.5 ul Pwo DNA polymerase (Roche), 0.5 ul of Hot-Start Taq polymerase (Qiagen), 1 ul of 100 uM oligonucleotide (LHA (5-CCATACGACGTCCCAGACTA-3'; SEQ ID NO: 7), identical to the sequence present at the 5'end of the sample RNAs) and water to 100 ul, was combined with 10 ul of beads, heated for 5 min at 95° C., and subjected to 2 reaction cycles (30 s at 95° C., 30 s at 56° C., 2 min at 72° C.). Beads were washed with 100 ul of the PCR buffer and eluted in 50 ul of the same buffer.

Figure 7:
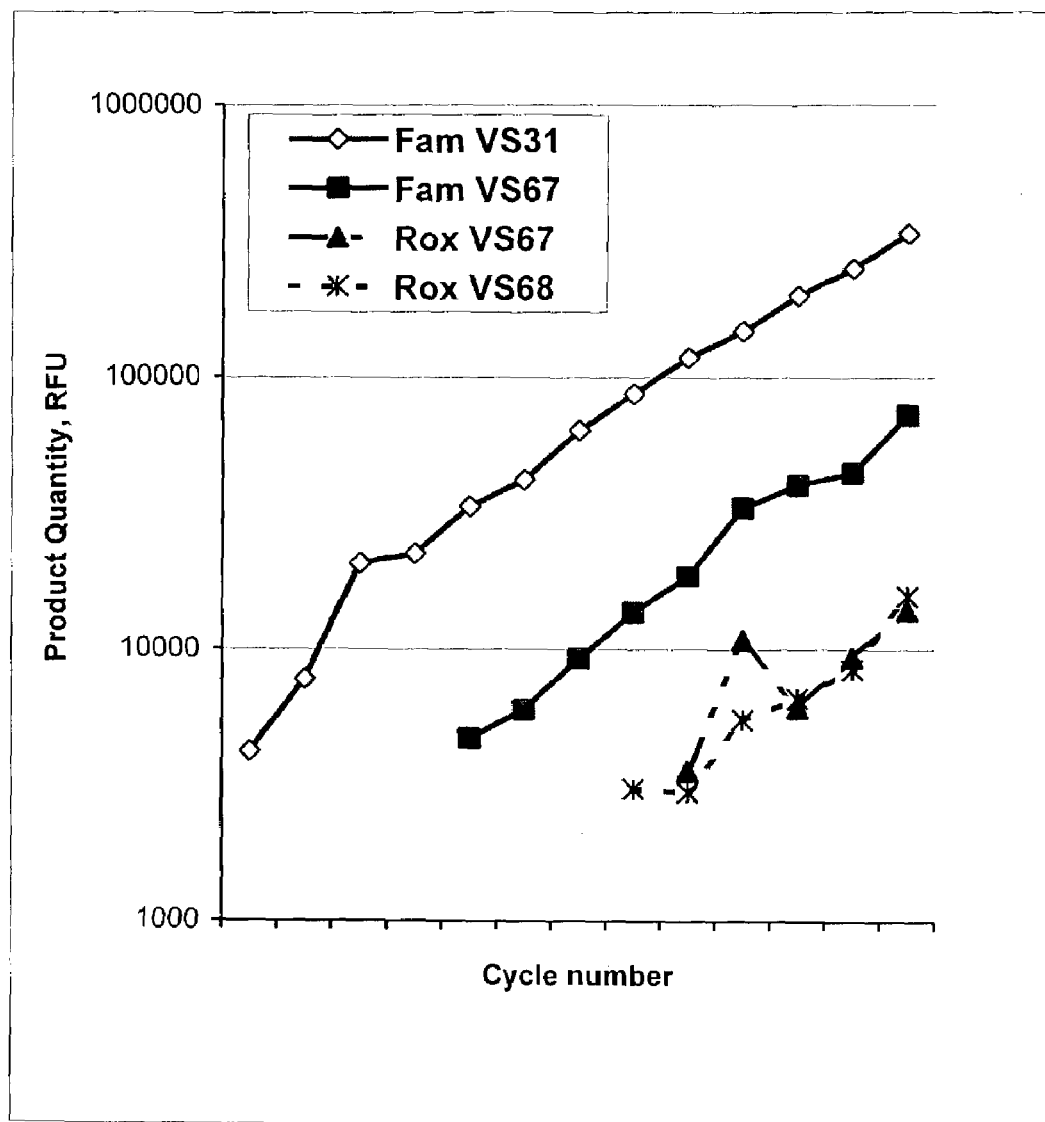
FIG. 7 shows the results of experiments testing the quantitative detection of multiple amplicons in a single amplification reaction.

PCR amplification: The PCR reaction was assembled as follows: 20 ul of the synthesized DNA, 8 ul of 10×PCR buffer, 3.2 ul of 25 mM MgCl2, 0.8 ul of 100 uM LHA primer, 1 ul of 100 uM LFAM primer (5'-labeled with FAM, 5'-CCGCGCCGAATAATATTAA-3'; SEQ ID NO: 5) and LROX primer (5'-labeled with ROX, 5'-CCCGGCGGATT ATTTATTA-3'; SEQ ID NO: 6), 0.5 ul of Taq polymerase, 0.5 ul of Pwo polymerase, 2 ul of 10 mM dNTPs, 65 ul of water; overlaid withmineral oil and amplified for 35 cycles (30 s at 95° C., 15 s at 60° C., 1 min 30 s at 72° C.). Starting with the cycle 15, reaction was paused after final step of each cycle to withdraw 10 ul aliquots and to replenish reaction with 10 ul of the reaction mixture (same composition as above with exception of sample DNA). Samples were supplemented with 1 ul of 50×TE buffer, diluted 10-fold with formamide, and denatured for 5 min at 95° C. before analysis performed on 96 capillary electrophoresis system (Spectrumedix). Quantities of PCR products were determined by integration of the peak areas on the chromatograms of the corresponding runs. The amplification curve shown in FIG. 7 was reconstructed by plotting PCR product quantity versus cycle number.

Example 2

Analysis of Differential Expression Using Known Quantities of Sample RNAs

Two samples of control RNAs were prepared in nuclease-free water:

sample 1 containing: VS31 RNA 53 pg/ul and VS32 RNA 42 pg/ul sample 2 containing: VS31 RNA 53 pg/ul and VS32 RNA 102 pg/ul.

3 ul of each sample were mixed with 1.25 ul 20 mM dNTP, 1 ul of 100 uM primer (JLFam (5'-CCGCGC-CGAATAATATTAAGCTCTAGCATTTAG-3'; SEQ ID NO: 8) for sample 1 and JLRox1 (5'-CCCGGCGGATTATT- TATTAGCTCTAGCATTTAG-3'; SEQ ID NO: 9) for sample 2) and nuclease free water to 10 ul. RNA was denatured for 2 min at 80° C. and cooled on ice. 15 ul of reaction mixture was added and incubated for 1 hour at 42° C.

RT Reaction Mixture:

| | |
|---|---|
| 5X buffer | 5 ul |
| 0.1 mM DTT | 2.5 ul |
| Superscript II RT (200 U/ul) | 0.5 ul (25 to 100 U depending on quantity of RNA) |
| 80% trehalose | 6.4 ul |
| 10 mg/ml BSA | 0.5 ul |
| SUPERase In (20 U/ul) | 1 ul |

Final composition of RT reaction: RNA, 50 mM Tris-HCl, pH 8.3, 75 mM KCl, 3 mM MgCl$_2$, 10 uM DTT, 50U SS II RT, 20% trehalose, 0.25 mg/ml BSA, 1 mM dNTP, 15.7% glycerol, 5 uM primer, 1U SUPERase In Destruction of RNA:

1U of RNAseH (Invitrogen) was added to each tube and incubated at 37° C. for 20 minutes followed by 75° C. for 15 minutes to kill the RNase H. 5 ul EXO-SAP-IT nuclease (USB) was added to the RT reaction and incubated for 20 minutes at 37° C. to destroy unused primers to avoid interference in subsequent PCR analysis, followed by 15 minutes at 80° C. to inactivate the enzyme.

Second Strand Synthesis:

5 ul of the RT reaction was combined with the SSS reaction mixture:

| | |
|---|---|
| 10X Vent buffer | 5.0 ul |
| 20 mM dNTP | 0.5 ul |
| DMSO | 1.0 ul |
| Q solution | 10 ul |
| 100 uM-HA | 0.5 ul |
| Vent Polymerase | 0.5 ul Vent DNA Polymerase (New England Biolabs) |
| water | 27.5 ul |

The second strand was prepared in thermocycler as indicated.

| | | | |
|---|---|---|---|
| 1X 94° C./5 min* | 50° C./5 min** | 68° C./5 min | *Add 2$^{nd}$ strand primer at 94° C. |
| 2X 95° C./2 min | 40° C./5 min | 68° C./5 min | **Add Vent at 72° C. |
| 1X 72° C./10 min | | | |

PCR Amplification:

20 ul of prepared cDNA were combined with:

| | |
|---|---|
| 10X Vent buffer | 7.0 ul |
| 20 mM dNTP | 0.7 ul |
| DMSO | 4 ul |
| Q solution (Qiagen) | 15.0 ul |
| LHA (100 mM) | 0.8 ul |
| LFAM2 primer (100 mM) | 1 ul (5'-labeled with Fam (Applied Biosystems) |
| LROX primer (100 mM) | 1 ul (5'-labeled with Rox (Applied Biosystems)) |
| Taq Polymerase (Qiagen) | 0.5 ul |
| Vent Polymerase | 0.5 ul |
| Water | to 100 ul |

Figure 8:
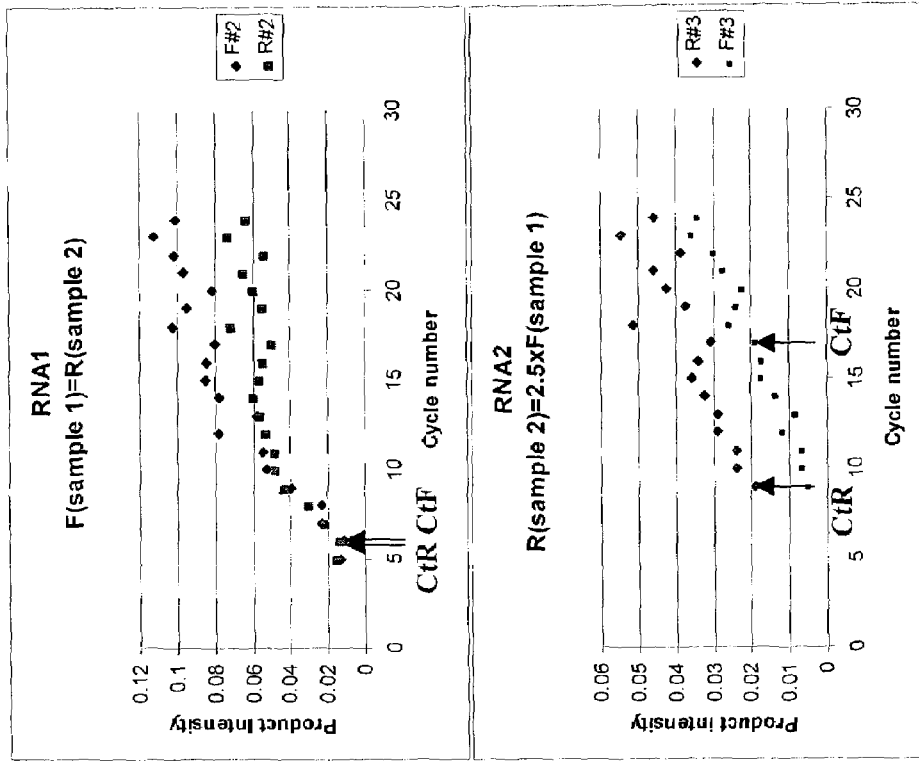
FIG. 8 shows the results of a differential expression analysis using known amounts of different RNAs.

The reaction mixtures were overlaid with mineral oil and subjected to PCR amplification for 35 cycles. (30 s at 95° C., 15 s at 60° C., 1 min 30 s at 72° C.). Starting with the cycle 15, reaction was paused after final step of each cycle to withdraw 10 ul aliquots and to replenish reaction with 10 ul of the reaction mixture (same composition as above with exception of sample DNA). Samples were supplemented with 1 ul of 50×TE buffer, diluted 10 fold with formamide, mixed with labeled DNA size standards (50–1000 bp, BioVentures) and denatured for 5 min at 95° C. before analysis performed on 96 capillary electrophoresis system (Spectrumedix). Quantities of PCR products were determined by integration of the peak areas on the chromatograms of the corresponding runs and normalized by the quantity of co-injected standard. The amplification curves shown in FIG. 8 were reconstructed by plotting PCR product quantity versus cycle number. The data are in agreement with the expected results, i.e., that the threshold cycle number ($C_t$) for VS31 RNA (RNA 1 in the figure) was the same between samples, and for VS32 RNA (RNA 2 in the figure), the $C_t$ for sample 2 is less than the $C_t$ for sample 1.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Polynucleotide Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference.

OTHER EMBODIMENTS

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for monitoring the amplification of a nucleic acid sequence of interest, said method comprising:

(a) contacting a nucleic acid sample with a first and a second oligonucleotide primer, wherein said first oligonucleotide primer specifically hybridizes with a nucleic acid molecule comprising said nucleic acid sequence of interest, and said second oligonucleotide primer specifically hybridizes with a sequence comprised by the complement of said nucleic acid sequence of interest, wherein the primer extension product of one oligonucleotide primer, when separated from its complement, can serve as a template for the synthesis of the extension product of the other primer;

(b) subjecting the mixture resulting from step (a) to an amplification regimen, said regimen comprising at least two cycles of nucleic acid strand separation, oligonucleotide primer annealing, and polymerase extension of annealed primers;

(c) removing an aliquot of said mixture, separating nucleic acid molecules in said aliquot, and detecting amplified product, wherein said removing is performed during said cycling regimen of step (b), following at least one of said cycles, wherein said separating nucleic acid molecules and said detecting incorporation is performed in real time during said regimen of step (b) and wherein said detection permits the monitoring of said amplification in real time.

2. The method of claim 1 wherein at least one oligonucleotide primer comprises a detectable label comprising a moiety selected from the group consisting of a light-absorbing dye, a fluorescent dye and a radioactive label.

3. The method of claim 2 wherein said detectable label comprises a fluorescent dye.

4. The method of claim 1 wherein step (c) is performed after each cycle in said amplification regimen.

5. The method of claim 1 wherein said separating nucleic acid molecules comprises capillary electrophoresis.

6. The method of claim 1 wherein said sample comprises products of a reverse-transcription reaction.

7. The method of claim 1 wherein said steps (a)–(c) are performed in a modular apparatus comprising a thermal cycler, a sampling device, a capillary electrophoresis device and a fluorescence detector.

8. The method of claim 7 wherein said modular device comprises a robotic arm.

9. The method of claim 1 wherein said monitoring permits the determination of the abundance of nucleic acid comprising said sequence of interest in said sample.

10. A method for monitoring the amplification of a set of nucleic acid sequences of interest, said method comprising:

(a) contacting a nucleic acid sample in a reaction vessel with a set of pairs of oligonucleotide primers, wherein:
each said pair comprises a first oligonucleotide primer that specifically hybridizes with a nucleic acid molecule comprising said nucleic acid sequence of interest, and a second oligonucleotide primer that specifically hybridizes a with a sequence comprised by the complement of said nucleic acid sequence of interest, wherein the primer extension product of one oligonucleotide primer, when separated from its complement, can serve as a template for the synthesis of the extension product of the other primer;

each said pair of oligonucleotides is specific for one nucleic acid sequence of interest; and each oligonucleotide primer pair in said set is selected so that it generates a distinctly sized amplification product in a subsequent amplification regimen;

(b) subjecting the mixture resulting from step (a) to an amplification regimen comprising at least two iterative cycles of nucleic acid strand separation, oligonucleotide primer annealing and polymerase extension of annealed primers, wherein during the amplification regimen, following at least one of said iterative cycles, an aliquot of said mixture is removed from said reaction vessel and nucleic acid molecules in said aliquot are separated;

(c) detecting a distinctly sized primer extension product present in said aliquot, wherein said detecting provides a real time profile of the amplification of said nucleic acid sequences of interest.

11. The method of claim 10 wherein at least one oligonucleotide in each said pair comprises a detectable label comprising a moiety selected from the group consisting of a light-absorbing dye, a fluorescent dye, and a radioactive label.

12. The method of claim 11 wherein said detectable label comprises a fluorescent dye.

13. The method of claim 10 wherein an aliquot is removed and nucleic acid molecules in said aliquot are separated and detected after each cycle in said amplification regimen.

14. The method of claim 10 wherein said separating nucleic acid molecules comprises capillary electrophoresis.

15. The method of claim 10 wherein said sample comprises products of a reverse-transcription reaction.

16. The method of claim 10 wherein said steps (a)–(c) are performed in a modular apparatus comprising a thermal cycler, a sampling device, a capillary electrophoresis device and a fluorescence detector.

17. The method of claim 16 wherein said modular device comprises a robotic arm.

18. The method of claim 10 wherein said monitoring permits the determination of the abundance of nucleic acids comprising said set of nucleic acid sequences of interest in said sample.

19. A method of monitoring the amplification of a set of nucleic acid sequences of interest, said method comprising:

(a) synthesizing a plurality of reverse transcription products by extension of a reverse transcription primer annealed to a template nucleic acid sample, wherein each of said reverse-transcription products comprises a common sequence tag comprised by said reverse-transcription primer;

(b) contacting said reverse-transcription products in a reaction vessel with (i) a set of oligonucleotide primers that recognize said set of nucleic acid sequences of interest, wherein each oligonucleotide primer is selected so that it generates a distinctly sized amplification product in a subsequent amplification regimen, and (ii) a detectably labeled oligonucleotide primer that comprises said common sequence tag;

(c) subjecting the mixture resulting from step (b) to an amplification regimen comprising at least two iterative cycles of nucleic acid strand separation, oligonucleotide primer annealing and polymerase extension of annealed primers, wherein during the amplification regimen, following at least one of said iterative cycles, an aliquot of said mixture is removed from said reaction vessel and nucleic acid molecules in said aliquot are separated;

(d) detecting the incorporation of said detectably labeled oligonucleotide primer in a distinctly sized primer extension product present in said aliquot, wherein said detecting provides a profile of the amplification of said set of nucleic acid sequences of interest.

20. The method of claim 19 wherein said detectably labeled oligonucleotide comprises a light absorbing dye, a fluorescent dye, or a radioactive label.

21. The method of claim 20 wherein said detectable label comprises a fluorescent dye.

22. The method of claim 19 wherein an aliquot is removed and nucleic acid molecules in said aliquot are separated and detected after each cycle in said amplification regimen.

23. The method of claim 19 wherein the aliquot removal, separating and detecting steps permit the real-time monitoring of said amplification.

24. The method of claim 19 wherein said separating nucleic acid molecules comprises capillary electrophoresis.

25. The method of claim 19 wherein said steps (a)–(d) are performed in a modular apparatus comprising a thermal cycler, a sampling device, a capillary electrophoresis device and a fluorescence detector.

26. The method of claim 25 wherein said modular device comprises a robotic arm.

27. The method of claim 19 wherein said monitoring permits the determination of the abundance of nucleic acids comprising said set of nucleic acid sequences of interest in said sample.

28. A method of monitoring the amplification of a set of nucleic acid sequences of interest, said method comprising:

(a) synthesizing a plurality of reverse transcription products by extension of a reverse transcription primer annealed to a template nucleic acid sample, wherein each of said reverse-transcription products comprises a first common sequence tag comprised by said reverse-transcription primer;

(b) synthesizing a complimentary cDNA strand using oligonucleotide primers comprising a common second sequence tag, wherein each oligonucleotide primer is selected so that it generates a distinctly sized amplification product in a subsequent amplification regimen.

(c) contacting the nucleic acid synthesis products of steps (a) and (b) in a reaction vessel with a set of oligonucleotide primers comprising oligonucleotides comprising said first and second common sequence tags;

(d) subjecting the mixture resulting from step (c) to an amplification regimen comprising at least two iterative cycles of nucleic acid strand separation, oligonucleotide primer annealing and polymerase extension of annealed primers, wherein during the amplification regimen, following at least one of said iterative cycles, an aliquot of said mixture is removed from said reaction vessel and nucleic acid molecules in said aliquot are separated;

(e) detecting a distinctly sized primer extension product present in said aliquot, wherein said detecting provides a profile of the amplification of said set of nucleic acid sequences of interest.

29. The method of claim 28 wherein at least one of said first and said second oligonucleotides comprises a detectable label comprising a moiety selected from the group consisting of a light-absorbing dye, a fluorescent dye and a radioactive label.

30. The method of claim 29 wherein said detectable label comprises a fluorescent dye.

31. The method of claim 28 wherein an aliquot is removed and nucleic acid molecules in said aliquot are separated and detected after each cycle in said amplification regimen.

32. The method of claim 28 wherein the aliquot removal, separating and detecting steps permit the real-time monitoring of said amplification.

33. The method of claim 28 wherein said separating nucleic acid molecules comprises capillary electrophoresis.

34. The method of claim 28 wherein said steps (a)–(e) are performed in a modular apparatus comprising a thermal cycler, a sampling device, a capillary electrophoresis device and a fluorescence detector.

35. The method of claim 34 wherein said modular apparatus comprises a robotic arm.

36. The method of claim 28 wherein said monitoring permits the determination of the abundance of nucleic acids comprising said set of nucleic acid sequences of interest in said sample.

37. A method for comparing the expression of a nucleic acid sequence of interest between a set of samples, said method comprising:
    (a) separately synthesizing a plurality of first strand cDNAs from each member of said set of samples using, for each sample, an oligonucleotide primer comprising a different sample-specific sequence tag;
    (b) mixing equal amounts of said first strand cDNAs from step (a);
    (c) contacting the mixture resulting from step (b) in a reaction vessel with oligonucleotide primers comprising:
        (i) a separate, distinguishably detectably labeled oligonucleotide primer corresponding to each sample-specific sequence tag used in step (a), wherein said primer comprises sufficient sequence comprised by said sample specific sequence tag to permit specific annealing of said primer to a nucleic acid molecule comprising said sample-specific tag;
        (ii) an oligonucleotide primer comprising sufficient sequence complementary to said nucleic acid sequence of interest to permit specific annealing of said primer to a nucleic acid molecule comprising said sequence of interest;
        wherein said primers corresponding to said sample-specific sequence tags and said primer comprising sequence complementary to said nucleic acid sequence of interest generate primer extension products that, when separated from their complements, can serve as template for the synthesis of a primer extension product of the other primer; and
    (d) subjecting the mixture of step (c) to an amplification regimen comprising at least two iterative cycles of strand separation, oligonucleotide primer annealing, and polymerase extension of the annealed primers;
    (e) removing, during said amplification regimen, after at least one of said iterative cycles, an aliquot from said reaction vessel, separating nucleic acids in said aliquot and detecting primer extension products comprising distinguishably detectably labeled oligonucleotide primer corresponding to each sample-specific sequence tag, wherein said separating nucleic acid molecules and said detecting incorporation is performed in real time during said regimen of step (d) and wherein said detection permits the monitoring of said amplification in real time;
    (f) comparing the detectable signals from said labels corresponding to said sample-specific tags, thereby comparing the expression of said gene of interest between said samples.

38. The method of claim 37 wherein said detectable label comprises a light-absorbing dye, a fluorescent dye, or a radioactive label.

39. The method of claim 38 wherein said detectable label comprises a fluorescent dye.

40. The method of claim 37 wherein said steps of removing an aliquot, separating nucleic acids in said aliquot and detecting primer extension products is performed after each cycle in said amplification regimen.

41. The method of claim 37 wherein said separating nucleic acid molecules comprises capillary electrophoresis.

42. The method of claim 37 wherein said steps (a)–(f) are performed in a modular apparatus comprising a thermal cycler, a sampling device, a capillary electrophoresis device and a fluorescence detector.

43. The method of claim 42 wherein said modular device comprises a robotic arm.

44. A method of monitoring the amplification of a set of nucleic acid sequences, said method comprising:
    (a) amplifying a set of nucleic acid sequences present in a set of reverse-transcription products wherein said amplifying comprises a regimen of at least two cycles of strand separation, oligonucleotide primer annealing and polymerase extension of the annealed primers, wherein each reverse transcription product in said set was made by extension of a reverse-transcription primer, said set of reverse transcription products comprising:
    one or more subsets of reverse-transcription products, wherein each subset comprises a plurality of reverse-transcription products from a single nucleic acid sample, wherein the members of each subset of reverse-transcription products comprise a sample-specific sequence tag incorporated into said reverse-transcription primer, wherein said amplifying comprises contacting said set of reverse-transcription products with two sets of oligonucleotide primers:
        (i) a set of gene-specific primers, wherein each gene specific primer in said set recognizes a specific nucleic acid sequence expressed in a nucleic acid sample, and wherein each gene specific primer in said set is selected so as to generate an amplification product that is distinct in size from amplification products generated with other gene specific primers in said set; and
        (ii) a set of sample specific primers, wherein each sample specific primer specifically hybridizes to a sample specific tag incorporated into a said reverse-transcription primer, and wherein each sample specific primer in said set of sample specific primers is distinguishably labeled;
    (b) during said regimen, following a primer extension step, removing an aliquot of the amplification mixture and separating nucleic acids in said aliquot; and
    (c) detecting incorporation of each sample specific primer in said aliquot;
wherein said detecting monitors, in each sample, in real time, the amplification of the set of nucleic acids recognized by said set of gene specific primers.

45. The method of claim 44 wherein said steps of removing an aliquot, separating nucleic acids in said aliquot and detecting primer extension products is performed after each cycle in said amplification regimen.

46. The method of claim 44 wherein said sample-specific primer is distinguishably labeled with a fluorescent dye, a light-absorbing dye, or a radioactive label.

47. The method of claim 46 wherein said sample-specific primer is distinguishably labeled with a fluorescent dye.

48. The method of claim 44 wherein said separating nucleic acid molecules comprises capillary electrophoresis.

49. The method of claim 44 wherein said steps (a)–(c) are performed in a modular apparatus comprising a thermal cycler, a sampling device, a capillary electrophoresis device and a fluorescence detector.

50. The method of claim 49 wherein said modular device comprises a robotic arm.

51. The method of claim 44 wherein said monitoring permits the determination of the abundance of nucleic acids comprising said set of nucleic acid sequences of interest in a sample from which said reverse-transcription products are made.

* * * * *

UNITED STATES PATENT AND TRADEMARK OFFICE
CERTIFICATE OF CORRECTION

PATENT NO. : 7,081,339 B2 Page 1 of 1
APPLICATION NO. : 10/387286
DATED : July 25, 2006
INVENTOR(S) : Slepnev It is certified that error appears in the above-identified patent and that said Letters Patent is hereby corrected as shown below:

TITLE PAGE, ITEM (54) + COL 1, LINES 1-3, SHOULD READ:

--METHODS FOR AMPLIFICATION MONITORING AND GENE EXPRESSION PROFILING, INVOLVING REAL TIME AMPLIFICATION REACTION SAMPLING--

Delete claims 10-36 at column 32, line 58 to column 35, line 25.

Delete claims 44-51 at column 36, line 26 to column 38, line 11.

Signed and Sealed this

Twelfth Day of December, 2006

JON W. DUDAS
*Director of the United States Patent and Trademark Office*